United States Patent
Badylak et al.

(10) Patent No.: US 6,375,989 B1
(45) Date of Patent: Apr. 23, 2002

(54) SUBMUCOSA EXTRACTS

(75) Inventors: Stephen F. Badylak; Andrew O. Brightman; Jason P. Hodde, all of West Lafayette, IN (US); Timothy B. McPherson, Granite City, IL (US); Sherry L. Voytik-Harbin, Zionsville, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/319,656

(22) PCT Filed: Dec. 10, 1997

(86) PCT No.: PCT/US97/22721

§ 371 Date: Jun. 10, 1999

§ 102(e) Date: Jun. 10, 1999

(87) PCT Pub. No.: WO98/25964

PCT Pub. Date: Jun. 18, 1998

Related U.S. Application Data

(60) Provisional application No. 60/032,685, filed on Dec. 10, 1996.

(51) Int. Cl.$^7$ .............................................. A61K 35/38
(52) U.S. Cl. ............................ 424/551; 514/2; 514/21
(58) Field of Search ............................. 424/551; 514/2, 514/21

(56) References Cited

U.S. PATENT DOCUMENTS

| | | |
|---|---|---|
| 4,743,552 A | 5/1988 | Friedman et al. |
| 4,801,299 A | 1/1989 | Brendel et al. ................ 623/1 |
| 4,829,000 A | 5/1989 | Kleinman et al. |
| 4,902,508 A | 2/1990 | Badylak et al. |
| 5,217,954 A * | 6/1993 | Foster et al. .................. 514/12 |
| 5,275,826 A | 1/1994 | Badylak et al. |
| 5,281,422 A | 1/1994 | Badylak et al. |
| 5,478,739 A | 12/1995 | Slivka et al. |
| 5,518,915 A | 5/1996 | Naughton et al. |
| 5,554,389 A | 9/1996 | Badylak et al. |
| 5,714,458 A * | 2/1998 | Adami et al. .................. 514/2 |

FOREIGN PATENT DOCUMENTS

| | | |
|---|---|---|
| WO | WO 96/24661 | 8/1996 |
| WO | WO 98/25549 | 6/1998 |

OTHER PUBLICATIONS

Hodde et al., Glycosaminoglycan Content of Small Intestinal Submucosa: A Bioscaffold for Tissue Replacement, *Tissue Engineering*, vol. 2, No. 3, 1996, pp. 209–217.

Cartlidge, S.A., and Elder, J.B., Transforming growth factor α and epidermal growth factor levels in normal human gastrointestinal mucosa. *British J. of Cancer*, vol. 60, No. 5, Nov. 1989, pp 657–660.

Vukicevic et al., Identification of Multiple Active Growth Factors in Basement Membrane Matrigel Suggets Caution in Interpretation of Cellular Activity Related to Extracellular Matrix Components. *Experimental Cell Research*, vol. 202, No. 1, Sep. 1992, pp 1–8.

Nice et al., The Major Colonic Cell Mitogen Extractable from Colonic Mucosa Is an N Terminally Extended Form of Basic Fibroblast Growth Factor. *J. of Biol. Chem.*, vol. 266, No. 22, Aug. 5, 1991, pp. 14425–14430.

Breen et al., *Methods in Carbohydrate Chemistry*. vol. 7, New York: Academic Press 1976, pp. 101–115.

Blumenkrantz, and Asboe–Hanson, Analytical Biochemistry, vol. 54, 1973, p. 484.

Linhardt, *Current Protocols in Molecular Biology*, New York: Wiley & Sons, 1994, unit 17 13 B.

Zohse et al., J. of Biol. Chem., vol. 267, pp 243–247, 1992.

Badylak S.T., Boder G.B., Morff R., Lantz G., Directed Connective Tissue Remodeling Upon a Biologic Collagen Substrate. *J. Cell Biochem.* Supplement 16F, p. 124, 1992.

Kuo C.Y., Burghen G.A., and Herrod H.G., Biohybrid Islet–Gland Equivalent for Transplantation. *Journal of Cellular Biochemistry*Supplement 18C, PZ110, Feb. 13–26, 1994.

Kleinman H.K., McGarvey M.L., Hassell J.R., Star V.L., Cannon F.B., Laurie G.W., and Martin G.R. Basement Membrane Complexes with Biological Activity, *Biochemistry* 25:312–318, 1986.

Freshney R.I. *Cultures of Animal Cells: A Manual of Basic Technique*. Chapters 12 and 13, pp. 155–185, Alan R. Liss, Inc.,New York, 1994.

El–Housseiny. E; et al., Orthotopic Implantation of Primary N–[4–(5–Nitro–2–furyl)–2–thiazoiyl]formamide–induced Bladder Cancer in Bladder Submucosa: An Animal Model for Bladder Cancer Study , *Cancer Research*, vol. 43:617–620, Feb. 1983.

Kashtan, H. et al., Intra–rectal injection of tumor cells: a novel animal model of rectal cancer, *Surgical Oncology*, 1:251–256, 1992.

Sigma 1994 Catalogue and Price List, Plant Cell Culture Equipment, p. 160.

Demain, *Manual Of Industrial Microbiology and Biotechnology*, pp. 249–262, American Society for Microbiology; Washington, D.C., 1986.

\* cited by examiner

Primary Examiner—Jean C. Witz
(74) *Attorney, Agent, or Firm*—Barnes & Thornburg

(57) ABSTRACT

A method for preparing a bioactive extract from warm-blooded vertebrate submucosal tissue is described. The submucosal tissue is extracted using an aqueous solution of extraction excipients, and the extracted bioactive components are then separated from the extraction excipients to provide an isolated extract enriched in bioactive components. The isolated extract is useful, inter alia, as additive for cell growth media to promote cell growth and proliferation in vitro.

27 Claims, 10 Drawing Sheets

SUBMUCOSA EXTRACTS

CROSS REFERENCE TO RELATED APPLICATIONS

This application is a Section 371(e) counterpart of International Application No. PCT/US97/22721, filed Dec. 10, 1997, which claims priority to U.S. Provisional Application Ser. No. 60/032,685, filed Dec. 10, 1996.

This invention was made with U.S. Government support under Grant #1 RO1 HD31425-01 awarded by the National Institute of Health. The U.S. Government has certain rights in the invention.

FIELD OF THE INVENTION

This invention relates to a bioactive extract or concentrate prepared from basement membranes of natural tissues and the use of those extracts to promote cell growth and proliferation. More particularly, this invention is directed to submucosal tissue extracts and their preparation and use in promoting cell growth in vitro and in vivo.

BACKGROUND AND SUMMARY OF THE INVENTION

It has been reported that various basement membranes and other extracellular matrices can be utilized as tissue graft constructs or as cell culture substrates. Several matrix products derived from complex substrates are commercially available for use in supporting cell growth in vitro. For example, Becton Dickinson currently offers two such products: Human Extracellular Matrix and MATRIGEL® Basement Membrane Matrix. Human Extracellular Matrix is a chromatographically partially purified matrix extract derived from human placenta and comprises laminin, collagen IV, and heparin sulfate proteoglycan. (Kleinman, HK et al., U.S. Pat. No. 4,829,000 (1989)) MATRIGEL® is a soluble basement membrane extract of the Engelbreth-Holm-Swarm (EHS) tumor, gelled to form a reconstituted basement membrane. Both of these matrix products require costly biochemical isolation, purification, and synthesis techniques and thus production costs are high.

Submucosal tissue harvested from warm blooded vertebrates is a collagenous matrix that has shown great promise as a unique graft material for inducing the repair of damaged or diseased tissues in vivo, and for inducing the proliferation and differentiation of cell populations in vitro. Submucosal tissue consists primarily of extracellular matrix material prepared by mechanically removing selected portions of the mucosa and the external muscle layers and then by lysing resident cells with hypotonic washes. Preliminary biochemical analyses show that the composition of small intestinal submucosa is similar to that of other basement membrane/extracellular matrix structures, and consists of a complex array of collagens, proteoglycans, glycosaminoglycans, and glycoproteins. The major components commonly identified in extracellular matrix tissues similar to submucosal tissue include the cell adhesion proteins, fibronectin, vitronectin, thrombospondin, and laminin; the structural components, collagens and elastin; and the proteoglycans, serglycin, versican, decorin, and perlecan.

Numerous studies have shown that submucosal tissue is capable of inducing host tissue proliferation, remodeling and regeneration of tissue structures following implantation in a number of in vivo microenvironments including lower urinary tract, body wall, tendon, ligament, bone, cardiovascular tissues and the central nervous system. Upon implantation, cellular infiltration and a rapid neovascularization are observed and the submucosa extracellular matrix material is remodeled into host replacement tissue with site-specific structural and functional properties.

Submucosal tissue can be obtained from various sources, including intestinal tissue harvested from animals raised for meat production, including, for example, pigs, cattle and sheep or other warm-blooded vertebrates. As a tissue graft, submucosal tissue undergoes remodeling and induces the growth of endogenous tissues upon implantation into a host. It has been used successfully in vascular grafts, urinary bladder and hernia repair, replacement and repair of tendons and ligaments, and dermal grafts. The preparation and use of submucosa as a tissue graft composition is described in U.S. Pat. Nos. 4,902,508; 5,281,422; 5,275,826; 5,554,389 and other related U.S. patents.

Direct interactions between extracellular matrix components and cells are known to mediate processes which are fundamental to migration, proliferation and differentiation during development. However, the role of the extracellular matrix in wound healing and tissue regeneration has been less well studied. It has been found in accordance with the present invention that submucosal tissue can be extracted to provide compositions comprising isolated bioactive components of the submucosal tissue in their active form. Such an enriched extract can be utilized as an additive for tissue culture media to promote in vitro cell growth and proliferation, and also can be used as an active ingredient for wound healing compositions such as topically applied creams and bandages.

DETAILED DESCRIPTION OF THE INVENTION

Definitions

Figure 1A:
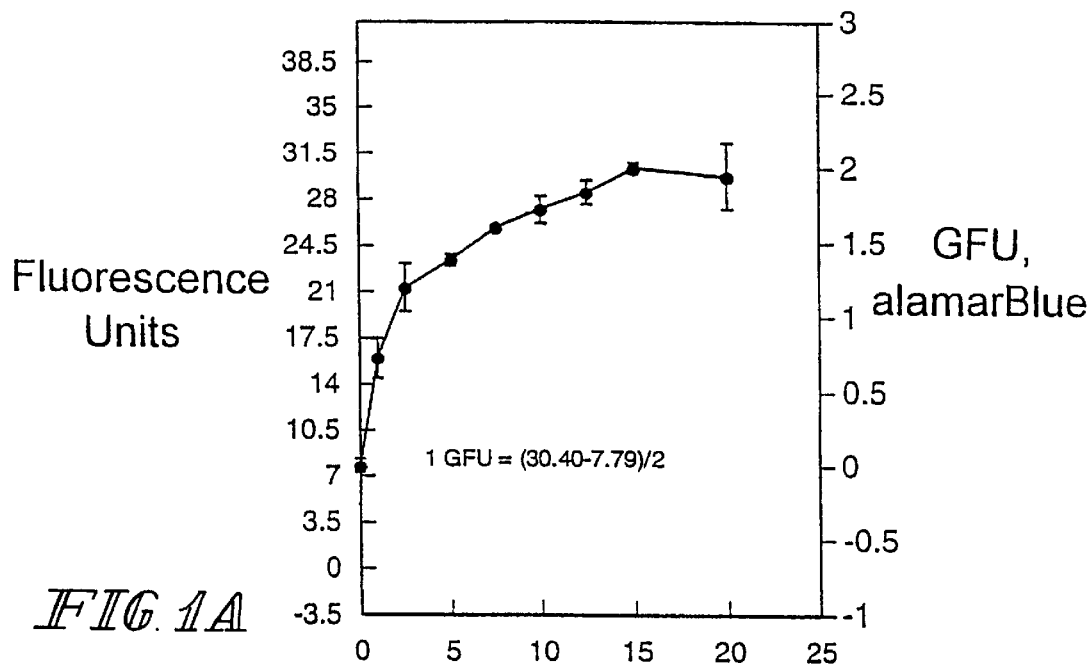
FIG. 1A and FIG. 1B. Comparison of Effects of Serum on 3T3 Fibroblasts in Two Growth Factor Assays. Neonatal calf serum standards were tested in alamarBlue assay for whole cell proliferation (●), see FIG. 1A, and [$^3$H]-thymidine incorporation assay for DNA synthesis (○), see FIG. 1B. Raw data units are fluorescence ($\lambda$=590) for alamarBlue assay and cpm/well ($\times 10^{-4}$) for [$^3$H]-thymidine. On the right axis the data are expressed as relative growth factor units (GFU) and the conversion equation is given. Each set of data points is the mean ±S.D. of triplicate samples from a single representative experiment.

Abbreviations used in the following text are defined as follows:
SIS: small intestinal submucosa;
FGF-2: basic fibroblast growth factor;
TGFβ: transforming growth factor beta;
GF: growth factor;
EGF: epidermal growth factor;
HEP: heparin;
HS: heparan sulfate;
HS: hyaluronic acid; and
PDGF: platelet derived growth factor.

As used herein the term bioactive component includes any compound, molecule or complex that induces, either directly or indirectly, a detectable cellular response upon contact of an effective amount of the compound or molecule with cells. A detectable cellular response includes a change in cell morphology, proliferation, growth, protein. or gene expression, etc. Collagen is not a bioactive agent in accordance with the term bioactive agent as defined herein.

The term extraction excipient as used herein relates to agents that disrupt the structure of macromolecules and also includes agents that assist in sequestering/separating compounds from one another based on the physical characteristics of those compounds.

The term chaotropic agent as used herein relates to an agent that disrupts the structure of macromolecules by interfering with intramolecular or intermolecular ionic or hydrogen bonding.

The term enriched as used herein refers an increase in the proportion of one or more components of a complex composition without addition of components form an external source. Accordingly, an enriched extract of submucosa tissue is an extract that contains a higher proportion of some of the original components of the source submucosa tissue relative to other original components of the source submucosal tissue.

A TGFβ-related factor is a compound exhibiting an activity profile similar to TGFβ (i.e. induction of a similar cellular response as TGFβ, in terms of cell growth, proliferation, morphology and protein expression upon contact of cell with the compound).

The present invention is directed in part to a bioactive extract and its method of preparation. The composition is prepared by extracting submucosal tissue with an aqueous solution of one or more extraction excipients to form an aqueous solution containing extracted submucosa bioactive components and the extraction excipients. The extracted bioactive components are then separated from the extraction excipients using art-recognized procedures to provide the bioactive composition.

The submucosal tissue used as the source and starting material for the bioactive compositions of the present invention comprises submucosa isolated from warm-blooded intestinal tissue as well as other tissue sources such as the alimentary, respiratory, urinary or genital tracts of warm-blooded vertebrates. The preparation of intestinal submucosa is described and claimed in U.S. Pat. No. 4,902,508, the disclosure of which is expressly incorporated herein by reference. Urinary bladder submucosa and its preparation is described in U.S. Pat. No. 5,554,389, the disclosure of which is expressly incorporated herein by reference. Stomach submucosa has also been obtained and characterized using similar tissue processing techniques. Such is described in U.S. patent application Ser. No. 60/032,683 titled STOMACH SUBMUCOSA DERIVED TISSUE GRAFT, filed on Dec. 10, 1996. Briefly, stomach submucosa is prepared from a segment of stomach in a procedure similar to the preparation of intestinal submucosa. A segment of stomach tissue is first subjected to abrasion using a longitudinal wiping motion to remove the outer layers (particularly the smooth muscle layers) and the luminal portions of the tunica mucosa layers. The resulting submucosa tissue has a thickness of about 100–200 micrometers, and consists primarily (greater than 98%) of acellular, eosinophilic staining (H&E stain) extracellular matrix material.

Preferred submucosal tissues for use as a source of bioactive compositions in accordance with this invention include intestinal submucosa, stomach submucosa, urinary bladder submucosa, and uterine submucosa. Intestinal submucosal tissue is one preferred starting material, and more particularly intestinal submucosa delaminated from both the tunica muscularis and at least the tunica mucosa of warm-blooded vertebrate intestine.

The isolated submucosal tissue is prepared for extraction in accordance with this invention by rinsing extensively with hypotonic solution to lyse any cells still associated with the submucosal matrix and to eliminate cell degradation products. Typically the submucosal tissue is comminuted before the extraction process. Preferably the submucosal tissue is frozen and pulverized under liquid nitrogen in an industrial blender and stored at −80° prior to the extraction process.

The comminuted submucosal tissue is extracted using an aqueous solution of one or more extraction excipients to provide an aqueous solution containing both the extracted bioactive components of the submucosa and the extraction excipients. The extractions are typically carried out at near neutral pH (about 5.5 to about 7.5) in the case of growth factor extraction and at acid pH during extraction of glycosaminoglycan components. The temperature of the solution during extraction is maintained between about 0 and about 50° C.

The extraction excipients utilized to form the aqueous solution for extracting the bioactive components from submucosal tissue in accordance with this invention include enzymes, and enzyme inhibitors, buffers, chaotropic salts, such as sodium chloride and magnesium chloride, and other chaotropic agents such as urea and guanidine. Typically the extraction excipients include at least a buffer and a chaotropic agent selected from the group consisting from urea, guanidine, sodium chloride, magnesium chloride, and non-ionic or ionic surfactants. When guanidine is used as a chaotropic agent, it is typically used at a concentration of about 2 to about 6M, most typically about 4M. Extraction solutions utilizing urea as the extraction excipient contain urea at a concentration of about 2 to about 8M, more preferably from about 2 to about 4M urea. Chaotropic salt solutions can be used at about 2 to about 8M. The extraction conditions, including the type and concentration of extraction excipients, are selected and optimized to solubilize the bioactive components without denaturing them during the process.

The bioactive submucosa extract of this invention is then formed by separating the extracted bioactive components in the solution from the extraction excipients using art-recognized procedures such as dialysis and/or chromatographic techniques. Preferably the extraction solution is dialyzed to reduce or remove the concentration of extraction excipients to provide a solution of the extracted bioactive components. Lyophilization of the resulting solution provides the bioactive composition of this invention as a stable lyophilizate.

The nature and quantity of the bioactive compounds contained in the composition of this invention is dependent on the nature and composition of the extraction excipients used for the extraction solution. Thus, for example, 2M urea in a pH 7.4 buffer provides an extracted fraction enriched for basic fibroblast growth factor and fibronectin, while 4M guanidine in the same buffer provides an extracted fraction enriched for a compound exhibiting an activity profile for transforming growth factor β.

Use of other extraction excipients provides bioactive extracts comprising proteoglycans, glycoproteins and glycosaminoglycans. Exemplary of such compounds are heparin, heparan sulfate, hyaluronic acid, chondroitin sulfate A and chondroitin sulfate B.

The normal process of tissue repair, whether regenerative or scar-forming, is characterized by a complex, multicomponent cascade of degradative and biosynthetic processes which are orchestrated by underlying cell-cell and cell-extracellular matrix interactions. These processes involve and/or are directed by a variety of cell types including monocyte/macrophage, fibroblasts and capillary endothelial cells. Secreted, circulating and extracellular matrix-bound growth factors work in concert to regulate cell migration, proliferation and differentiation throughout the repair process. For example, PDGF, EGF, TGFα, TGFβ and FGF-2 are just a few in an ever increasing list. Similar to the tissue development which occurs during embryonic and fetal growth, the events of tissue repair are mediated through interactions between cells, extracellular matrix molecules and growth factors. From studies on the process of tissue remodeling it is now clear that growth factors regulate the synthesis and deposition of extracellular matrix components and, in turn, these synthesized extracellular matrix components regulate the availability and activity of the growth factors.

The process of tissue regeneration as opposed to scar formation in response to tissue injury can be enhanced by the implantation of various biomaterials. The field of tissue engineering has focused on the development of naturally occurring and/or synthetic materials for tissue replacement or augmentation of wound repair. The bioactive compositions prepared in accordance with this invention can promote cell growth and proliferation in vitro and in vivo. Thus the composition can be optionally sterilized and used as an additive either for nutrient media for cell tissue culture or as an ingredient for wound healing compositions. Thus, for example, the composition can be added to a cream base in an amount effective to promote healing to provide a topical ointment for application to wounds to promote healing. Alternatively, a solution of the bioactive compositions in accordance with the present invention can be applied to the wound contacting portions of bandages or other wound dressings which can then serve as a carrier for delivery of the bioactive compositions to wounds in an amount effective to promote wound healing.

Furthermore, observing the repair of wounds treated with components of submucosal tissue relative to untreated control wounds will provide an opportunity to study the fundamental principles of wound healing. An initial understanding of the composition of active factors present in this biomaterial is critical to the investigation of the biochemical signals and responses being exchanged with the host tissues. As well, the identification of both a TGFβ-related protein FGF-2 along with other bioactive components in extracts of submucosal tissue provides insights into the mechanisms behind the novel properties of submucosal tissue as a wound healing and tissue regenerative biomaterial.

The isolated extracts of the present invention can be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly alter the bioactivity of the submucosal tissue components is preferably used. Preferred sterilization techniques include exposing the graft to peracetic acid, low dose gamma irradiation (2.5 mRad) and gas plasma sterilization.

Submucosa Growth Factors

Submucosal tissue was extracted with four different aqueous solvents and the extracts were evaluated for their effects on Swiss 3T3 fibroblasts. Two, in vitro, assays were used in parallel for the detection of factors capable of stimulating either whole cell proliferation or DNA synthesis. Specific antibodies directed against FGF-2 and TGFβ were used to confirm the identity of these growth factors as major fibroblast stimulating factors extractable from submucosal tissue. This represents the first demonstration of growth factors isolated from the submucosal tissue of the intestine.

When used as a biomaterial for tissue replacement, submucosal tissue induces site-specific tissue remodeling. To determine the components of submucosa tissue that induce tissue remodeling, submucosal tissue has been extracted and the extracts tested for the ability to stimulate Swiss 3T3 fibroblasts to synthesize DNA and proliferate. Each of the different extracts of submucosal tissue had measurable growth stimulating activity when analyzed in both a whole cell proliferation assay (alamarBlue dye reduction) and a DNA synthesis assay ([$^3$H]-thymidine incorporation). Proteins extracted from submucosal tissue with 2 M urea induced activity profiles in the two assays which were very similar to the activity profiles of basic fibroblast growth factor (FGF-2) in the assays. As well, the changes in cell morphology in response to the extracted proteins mimicked the changes induced by FGF-2. Neutralization experiments with specific antibodies to this growth factor confirmed the presence of FGF-2 and indicated that it was responsible for 60% of the fibroblast stimulating activity of the urea extract of submucosal tissue.

Figure 6:
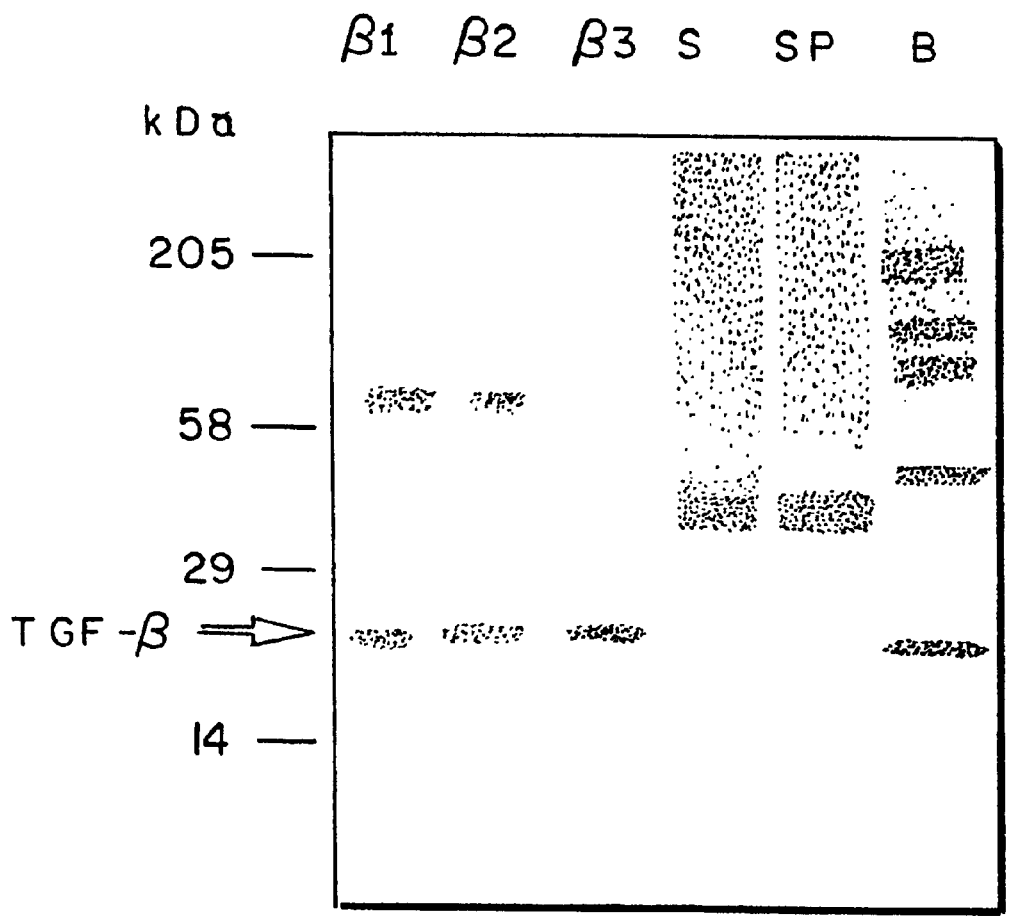
FIG. 6. A Drawing Representing the Immunodetection of TGFβ-related Protein in an Extract of SIS. TGFβ standards β1 (10 ng), β2 (20 ng), β3 (20 ng), 40 ug of guanidine extracts of bovine bone (B) and 160 ug of porcine SIS (S), and 200 ug of an active fraction, partially purified from a guanidine extract of SIS by column chromatograph (SP), were separated on 4–20% SDS-PAGE and electro-blotted to PVDF paper. Detection of TGFβ was with an affinity purified pan-specific polyclonal antibody to TGFβ (1:1,000). Secondary antibody coupled to HRP was at 1:15,000.

Western blot analysis with a monoclonal antibody specific for FGF-2 detected a reactive doublet at approximately 19 kDa and further confirmed the presence of FGF-2. The activity of proteins extracted from submucosal tissue with 4 M guanidine was partially neutralized by a transforming growth factor β (TGFβ) specific antibody. Changes in the morphology of the fibroblasts exposed to this extract were similar to changes induced by TGFβ. Although no reactive protein band was detected at 25 kDa in a nonreduced western blot analysis, several bands were reactive at higher molecular weight (see FIG. 6). The identity of this TGFβ-related component is unknown. Identification of FGF-2 and TGFβ-related activities in submucosal tissue (FGF-2 and TGFβ are known to significantly affect critical processes of tissue development and differentiation) provides the opportunity to prepare compositions for enhancing wound healing and tissue remodeling.

Submucosa Glycosaminogycans

Glycosaminoglycans (GAGs) are important components of extracellular matrices, including submucosal tissue, and therefore extractions were performed to identify the species of glycosaminoglycans present in submucosal tissue. Since GAGs represent the post-translational glycosylation of proteoglycan core proteins, it is anticipated that a variety of proteoglycans will be found in submucosal tissue. Glycosaminoglycans serve both structural and functional roles in extracellular matrices. In addition to providing structural integrity to the extracellular matrix, GAGs modulate the healing of soft tissues in several different ways. Such modulation includes organizing the deposition of collagen fibers, stimulating angiogenesis, inhibiting coagulation, and initiating cell and tissue proliferation and differentiation.

During wound healing, growth factor-GAG interactions abound. Heparin chains may directly stimulate angiogenesis or may act as a part of a proteoglycan to stimulate the angiogenic effects of FGF-2. Chondroitin sulfate B, as a component of several different proteoglycans, interacts with TGF-β and may help to control matrix formation and remodeling during the later phases of healing. In addition to regulating the function of TGF-β1, chondroitin sulfate B containing proteoglycans regulate the structure of the extracellular matrix by controlling collagen fibril size, orientation, and deposition.

Intestinal submucosal tissue was chemically extracted and the extracts were analyzed. The extractable uronic acid content was determined to be 47.7 μmol/g (approximately 21 μg GAG/mg) of the dry weight of the submucosal tissue. Using electrophoretic separation of GAGs on cellulose acetate membranes, hyaluronic acid, heparin, heparan sulfate, chondroitin sulfate A and chondroitin sulfate B (chondroitin sulfate B is also known as dermatan sulfate) were identified. Digestion of specific GAGs with selective enzymes confirmed the presence of these GAG species. Two GAGs common to other tissues with large basement membrane extracellular matrix components, keratan sulfate and chondroitin sulfate C, were not detected in the submucosal tissue extracts.

The remodeling phenomenon which occurs in mammals following implantation of submucosal tissue includes rapid neovascularization and early mononuclear cell accumulation. Mesenchymal and epithelial cell proliferation and differentiation are typically observed by one week after in vivo implantation and extensive deposition of new extracellular matrix occurs almost immediately. The role of submucosal tissue GAGs in these processes remains unclear, however individual GAGs are known to perform critical cell functions.

For example, FGF-2 requires heparin or heparan sulfate containing molecules for high affinity binding to its receptor. Once bound to its receptor, FGF-2 induces angiogenesis, cell differentiation and cell proliferation. In similar fashion, heparin has also been shown to potentiate EGF and PDGF-induced fibroblast proliferation, and heparin, heparan sulfate, and chondroitin sulfate B have recently been shown to inhibit the binding of insulin-like growth factor-I (IGF-1) to its binding proteins. It is plausible that such growth factors are bound to the GAGs of submucosal tissue, or are attracted to the GAGs of submucosal tissue after implantation, given the morphologic observations of angiogenesis and cell proliferation reported in numerous in vivo studies.

Hyaluronic acid has been hypothesized to sequester TGF-β1 in the extracellular matrix. In fetal wounds, it has also been associated with tissue regeneration and the rapid, highly organized deposition of collagen. High levels of hyaluronic acid in healing tissues have been associated with scarless wound repair, leading to the postulation that the sequestering of TGF-β1 by hyaluronic acid may inhibit the formation of scar tissue. It is plausible that the levels of hyaluronic acid in submucosal tissue are adequate to bind the amount of TGF-β1 locally released in response to injury, thus explaining the paucity of scar tissue deposition and the subsequent tissue remodeling seen in response to submucosal tissue implantation in vivo.

Chondroitin sulfate B can interact with growth factors as a part of an antithrombotic agent (but also has independent activity as an antithrombotic agent) by inhibiting the thrombin induced aggregation of platelets and may activate the fibrinolytic pathway by causing the release of tissue plasminogen activator (tPA). Chondroitin sulfate B can act as an anticoagulant by inhibiting thrombin formation, either directly through heparin cofactor II or antithrombin II or indirectly through protein C activation. In previous vascular studies in which submucosal tissue was used as large and small diameter arterial and venous grafts, thrombosis was not a significant problem when the stratum compactum was used as the blood contact surface. It is plausible that chondroitin sulfate B or a chondroitin sulfate B containing proteoglycan present in the material contributes to the thromboresistant properties that have been observed.

Submucosa Fibronectin

Fibronectin (Fn) is a large dimeric protein of the plasma and extracellular matrix with a molecular weight of approximately 440 kDa. Fn is among the first proteins deposited in new extracellular matrix and has chemotactic and cell adhesive activities for a variety of cells, including fibroblasts and endothelial cells. As these cells are important in wound healing and tissue remodeling, Fn may play a pivotal role in the recruitment and retention of host cells to the wound site. Fn comprises approximately 0.1% of the dry weight and is distributed throughout the thickness of submucosal tissue.

Extraction of submucosal tissues with a buffer containing 2 M urea, 2.5 mg/ml heparin, 50 mM Tris, at pH 7.5 produces an extract that is enriched in fibronectin. This composition can be used for in vivo applications as a chemotactic agent for attracting selected cell populations to a desired site. For example, a submucosal tissue extract enriched in fibronectin can be used by itself or in combination with other submucosal tissue extracts, or in combination with other bioactive molecules, to prepare compositions that induce and retain host cells at the site of implantation to assist in the repair of damaged or diseased tissues.

In accordance with one embodiment of the present invention submucosal tissue of a warm blooded vertebrate is used to prepare an extract enriched for a bioactive component of said submucosal tissue. The extract preparation comprises the steps of extracting submucosal tissue with an aqueous solution of extraction excipients to form an aqueous solution of extracted bioactive components and extraction excipients, and separating the extracted bioactive components from the extraction excipients to form a bioactive concentrate composition. The isolated extract can be lyophilized to form a dry powder form of the extract or can be used in its aqueous form. In one embodiment the extract is used to induce the growth and proliferation of cells in vitro or in vivo.

In one embodiment the submucosa extracts of the present invention are combined with nutrients, including minerals, amino acids, sugars, peptides, proteins, or glycoproteins that facilitate cellular proliferation, such as laminin and fibronectin and growth factors such as epidermal growth factor, or platelet-derived growth factor. In one preferred embodiment lyophilized powder forms of the submucosal extract can be used to supplement standard eukaryotic or prokaryotic culture media to enhance the standard media's capacity for sustaining and inducing the proliferation of cells cultured in vitro. More particularly, the submucosa extracts of the present invention can be used with commercially available cell culture solid and liquid media (both serum based and serum free). Cells cultured on substrates comprising submucosa extracts can either be in direct contact with the submucosal extract substrate or they can simply be in fluid communication with the submucosal extract substrate. It is anticipated that the cell growth compositions of the present invention can be used to induce the differentiation of undifferentiated cells as well as support the growth of differentiated cells while maintaining the differentiated state of such cells.

The submucosa extracts of the present invention can also be used in combination with implantable compositions or prostheses to induce the proliferation of endogenous cells and stimulate the repair of damaged or diseased tissues in vivo. The submucosa extracts can be combined with pharmaceutically acceptable carriers or excipients to enhance the delivery and contact of the submucosa extract bioactive components with the desired tissues in vivo. For example, the submucosa extracts can be formulated as an ointments, creams, or gels for topical administration, or for coating bandages, gauze or sutures. Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (isolated extract) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (isolated extract) customarily is added to an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (isolated extract) is added to the formulation at the desired concentration at a point preceding addition of the gelling agent.

The method for preparing a bioactive extract of submucosal tissue that is useful for promoting cell growth comprises the steps of extracting submucosal tissue with an aqueous solution of extraction excipients to form an aqueous solution of extracted bioactive components and extraction excipients, and separating the extracted bioactive components from the extraction excipients to form the bioactive extract. The extraction excipient is an enzyme, enzyme inhibitor or a chaotropic agent or combination thereof, wherein the chaotropic agent is urea, guanidine, sodium chloride, magnesium chloride, ionic or non-ionic surfactants or combination thereof.

A submucosa extract can be prepared that is enriched for a preselected natural component by selection of the appropriate extraction conditions. The extraction conditions, including the type and concentration of extraction excipients, are selected and optimized to solubilize the bioactive components without denaturing them during the process. For example, 2M urea in a pH 7.4 buffer provides an extracted fraction enriched for basic fibroblast growth factor and fibronectin, while 4M guanidine in the same buffer provides an extracted fraction enriched for a compound exhibiting an activity profile for transforming growth factor β. Similarly the extraction conditions can be selected to isolate an extract enriched for fibronectin or a glycosaminoglycan, including chondroitin sulfate A, chondroitin sulfate B (dermatan sulfate), heparin, heparan sulfate or hyaluronic acid all of which exist in the native submucosal tissue.

EXAMPLE 1

Extraction of FGF-2 and TGFβ-related Proteins

Materials alamarBlue was obtained from Alamar Bioscience Inc. (Sacramento, Calif.). [$^3$H]thymidine (64.0 Ci/mmol) and enhanced chemiluminescense (ECL) reagents were purchased from Amersham Life Science Inc. (Arlington Heights, Ill.). Bovine recombinant FGF-2 was purchased from Boehringer Mannheim (Indianapolis, Ind.). Purified porcine PDGF, recombinant human EGF, porcine TGFβ1, pan-specific, TGFβneutralizing antibody and FGF-2 neutralizing antibody were purchased from R&D Systems (Minneapolis, Minn.). Recombinant human TGFβ3 standard was purchased form Calbiochem. Purified recombinant human FGF-2 and monoclonal antibody to FGF-2 were generously provided by Dr. Brad Olwin, Purdue University.

Cells

Swiss 3T3 mouse fibroblasts were obtained from American Type Culture Collection (Bethesda, Md.). Cells were propagated in Dulbecco's modified Eagle's medium (DMEM) (Sigma, St. Louis, Mo.) containing 4.5 g/L glucose, 2 mM glutamine, 1.5 gL $NaHCO_3$, 100 U/ml penicillin, 100 µg/ml streptomycin, and 10% neonatal calf serum (NNCS) (Sigma, St. Louis, Mo.). Cells were grown in 75 $cm^2$ culture flasks and maintained in a humidified atmosphere of 5% $CO_2$ at 37° C. Subcultures were established every 3–4 days to prevent cells from exceeding 75% confluency. Cells representing limited passage numbers 9–13 were used for all assays.

Small Intestinal Submucosa

Small intestinal submucosa (SIS) was prepared from porcine intestine obtained from a local meat processing plant. Intestine was rinsed free of contents, everted and the superficial layers of the mucosa were removed by mechanical delamination. The tissue was reverted to its original orientation and the external muscle layer removed. The prepared SIS tube was split open longitudinally and rinsed extensively in water to lyse any cells associated with the matrix and to eliminate cell degradation products. Immediately after rinsing, SIS was frozen in liquid nitrogen and stored at −80° C. Frozen tissue was sliced into 1 cm cubes, pulverized under liquid nitrogen with an industrial blender to particles less than 2 $mm^2$ and stored at −80° C. prior to use.

Preparation of Extracts of SIS

Extraction buffers used for these studies included 4 M guanidine, 2 M urea, 2 M $MgCl_2$ and 2 M NaCl each prepared in 50 mM Tris-HC1, pH 7.4. SIS powder was suspended in extraction buffers (25% w/v) containing phenylmethyl sulphonyl fluoride, N-ethylmaleimide, and benzamidine (protease inhibitors) each at 1 mM and vigorously stirred for 24 hours at 4° C. The extraction mixture was then centrifuged at 12,000 xg for 30 minutes at 4° C. and the supernatant collected. The insoluble material was washed briefly in the extraction buffer, centrifuged, and the wash combined with the original supernatant. The supernatant was dialyzed extensively in Spectrapor tubing (MWCO 3500, Spectrum Medical Industries, Los Angeles, Calif.) against 30 volumes of deionized water (9 changes over 72 hours). The dialysate was centrifuged at 12,000 xg to remove any insoluble material and the supernatant was used immediately or lyophilized for long term storage.

alamarBlue Assay alamarBlue is a metabolic indicator dye. As a redox indicator, alamarBlue is reduced by reactions of normal cellular metabolism and provides an indirect measure of viable cell number. This assay has been recently described (Voytik-Harbin et. al., In Vitro Cell Dev Biol, 1997) and is presented here in brief. Swiss 3T3 fibroblasts were seeded into 96-well plates at 8,000 cells/ml in DMEM (200 µl) containing 1% neonatal calf serum (NNCS). After incubation for 24 hours, standards and test substances were added to each well (50 µl). Following incubation for an additional 72 hours, each well was examined microscopically to observe cell viability, number, and morphology. The medium was removed and fresh medium containing 1% NNCS and 10% alamarBlue was added to each well. After 18–20 hours, dye reduction was monitored spectrofluorometrically using a LS-50B Luminescence Spectrometer (Perkin Elmer, Norwalk, Conn.) with excitation and emission wavelengths of 560 nm and 590 nm, respectively. All samples were assayed in triplicate. Background fluorescence measurements were determined from wells containing dye reagent in culture medium but no cells. The mean and standard deviation for all fluorescence measurements were calculated and subsequently corrected for background. One growth factor unit (GFU) was defined as half of the maximal response to serum (NNCS) above unstimulated background.

$[^3H]$-Thymidine Incorporation Assay

Mitogenic activity was quantitated by measuring incorporation of $[^3H]$-thymidine during DNA synthesis. Swiss 3T3 fibroblasts were seeded into 96-well plates at 14,000 cells/nl in 200 µl of complete DMEM containing 10% NNCS. The cells were grown to confluency (approximately 72 hours) in a 5% $CO_2$ incubator at 37° C., at which time the medium was changed to DNEM containing 2% NNCS. Following incubation for 24 hours, standards or test substances (50 µl) were added to each well. After an additional 24 hour incubation, 1 µCi of $[^3H]$-thymidine in 20 µl phosphate buffered saline (PBS), pH 7.4 was added to each well. Four hours later, the medium was removed and the cells were treated with 0.1% trypsin (100 µl) by incubation at 37° C. for at least 10 minutes. The cells were harvested onto glass fiber filters using a 290 PRD Cell Harvester (Cambridge Technology Inc., Watertown, Mass.), washed repeatedly with water, and then rinsed with 70% ethanol. The filters were air dried and placed in 5 ml EcoLite (ICN, Costa Mesa, Calif.) liquid scintillant for radioactivity determination using a 1900TR Packard Liquid Scintillation Analzyer (Canberra Co., Meriden, Conn.). All standards and test substances were assayed in triplicate and the mean and standard deviations calculated. One GFU was defined as half of the maximal response to serum (NNCS) above unstimulated background.

Neutralization with Specific Antibodies

Dose-response patterns for TGFβ, FGF-2, PDGF, EGF and SIS extracts were generated in both $[^3H]$-thymidine and alamarBlue assays. The lowest concentration of each factor or extract which gave the greatest response in the assays was used for neutralization studies. Extracts or purified growth factors were incubated for 1 hour at 37° C. in the absence or presence of specific neutralizing antibodies at antibody concentrations ranging from 0.5 µg/ml to 200 µg/ml. Bioactivity of the neutralized samples was then analyzed in both the $[^3H]$-thymidine and alamarBlue assays.

Immunodetection of FGF-2 and TGFβ

Extracts were mixed with sample buffer and separated on 4–20% gradient or 16.5% SDS-PAGE. The proteins were transferred to polyvinylidene difluoride membrane (PVDF) paper in 10 mM CAPS buffer, 10% methanol, 1.3 mM SDS in a wet transfer system at 500 mA for 4 hours at 4° C. Blots were blocked with 5% dry milk. 0.05% Tween-20 in PBS for 2 hours at room temperature or overnight at 4° C. Primary antibodies were diluted in 1% bovine serum albumin (BSA), 0.05% Tween-20 in PBS (BTP buffer) and were incubated with the blots for 2 hours at 37° C. The blots were washed with 0.05% Tween-20 in PBS. Secondary antibodies coupled to horseradish peroxidase (HRP) were diluted in BTP buffer and incubated with blots for 1 hour at room temperature. After final washing, the blots were incubated with enhanced chemiluminescense (ECL) reagents and exposed to hyperfilm-ECL as directed by the manufacturer (Amersham Life Science Inc., Arlington Heights, EL). Specific dilutions for antibodies are described in the Brief Description of the Drawings.

RESULTS: Growth Factor Activity Extracted from Small Intestine Submucosa

Figure 1B:
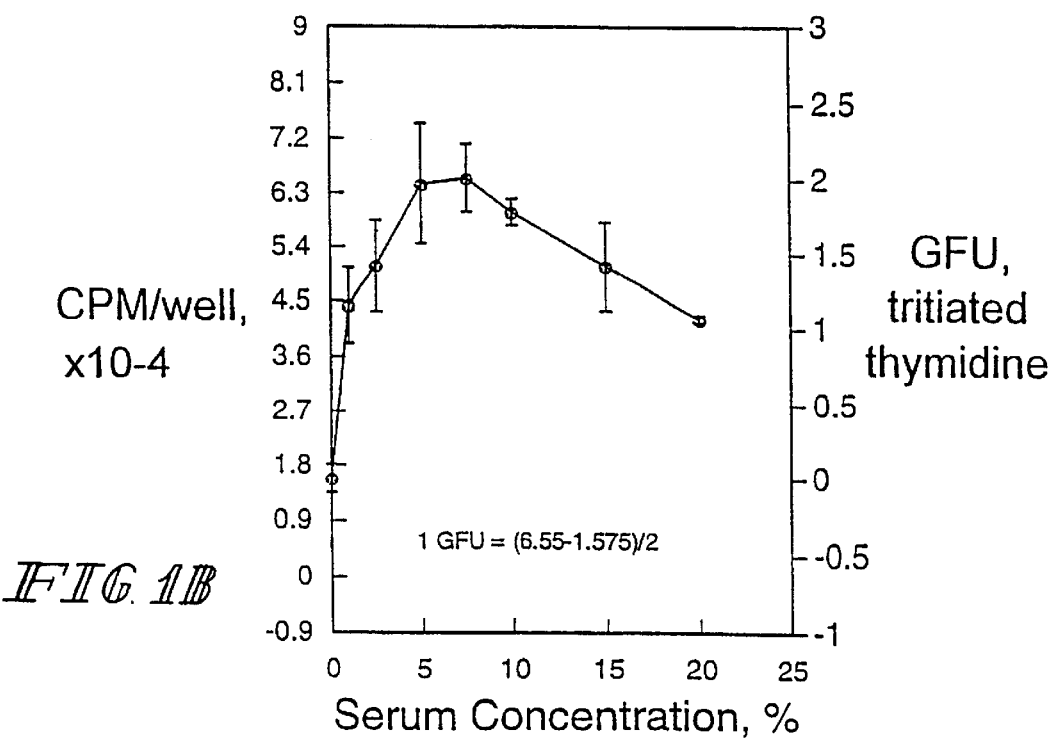

Several chaotropic aqueous solvents were selected to extract potential growth factors from SIS. Extraction of powdered SIS tissue with high concentrations of guanidine, urea, NaCl or MgCl$_2$ under neutral buffer conditions was effective in removing growth factor activity. Dose-response curves comparing the different extracts in two in vitro bioassays demonstrated the utility of multiple assays and multiple extractions. The two assays provided distinct and complementary information. The more traditional mitogen assay ([$^3$H]-thymidine incorporation) measured the stimulation of DNA synthesis of a confluent, quiescent monolayer of fibroblasts. In complement, the whole cell proliferation assay (alamarBlue dye reduction) measured indirectly the increase in cell number from a low density, quiescent population of fibroblasts. Both bioassays were standardized using neonatal calf serum in standard curves and results were expressed as relative growth factor units, GFU (See FIG. 1A and 1B).

Figure 2A:
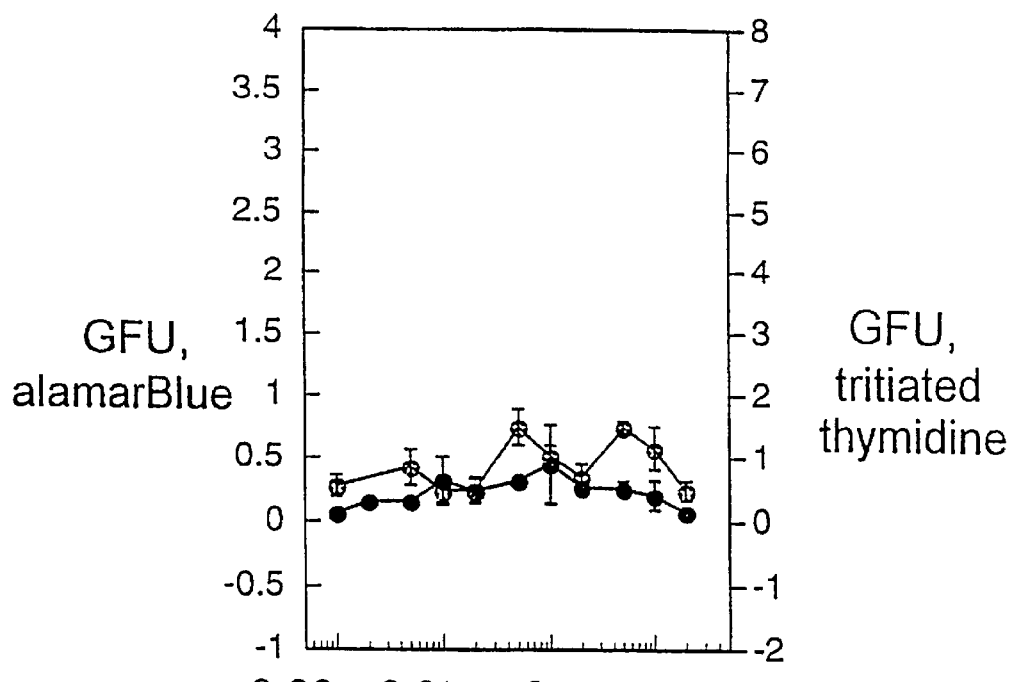
FIG. 2A–FIG. 2D. Responses to Purified Growth Factors in the Bioassays. The response of 3T3 fibroblasts to several GFs were determined by measuring whole cell proliferation (alamarBlue assay, ○, left axis) and DNA synthesis ([$^3$H]-thymidine assay, ○, right axis). Commercially available porcine TGFβ1 (FIG. 2A), bovine FGF-2 (FIG. 2B), porcine PDGF (FIG. 2C), and human EGF (FIG. 2D) were tested over a range of concentrations known to be effective with fibroblasts.
Figure 2B:
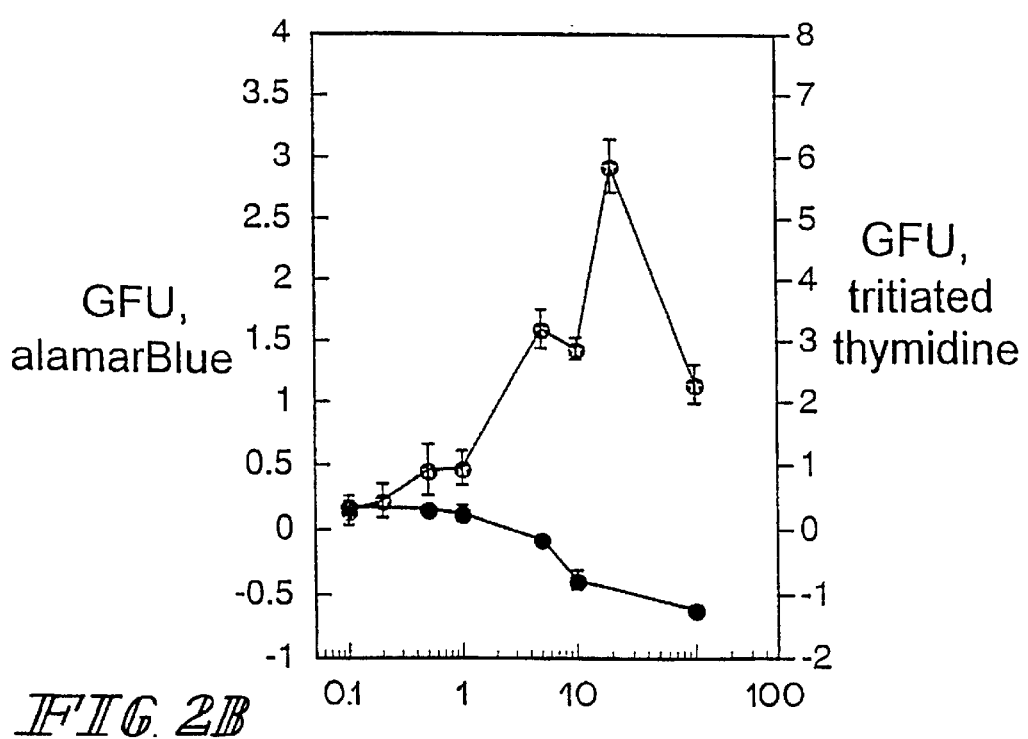
Figure 2C:
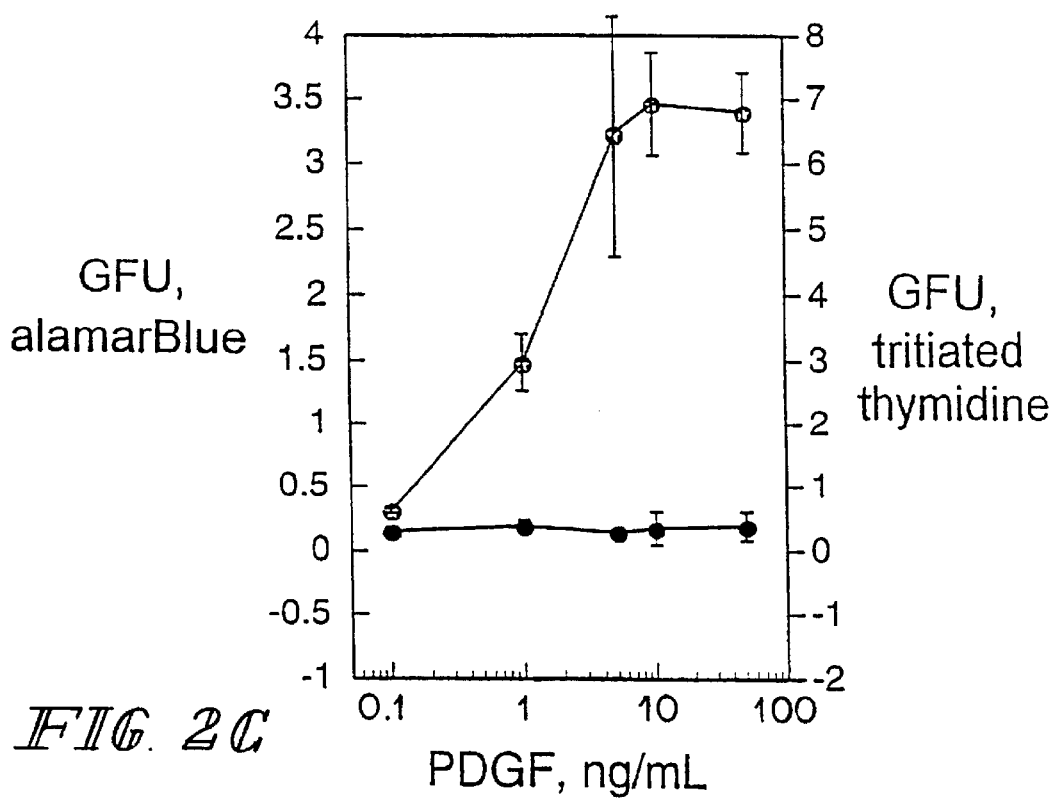
Figure 2D:
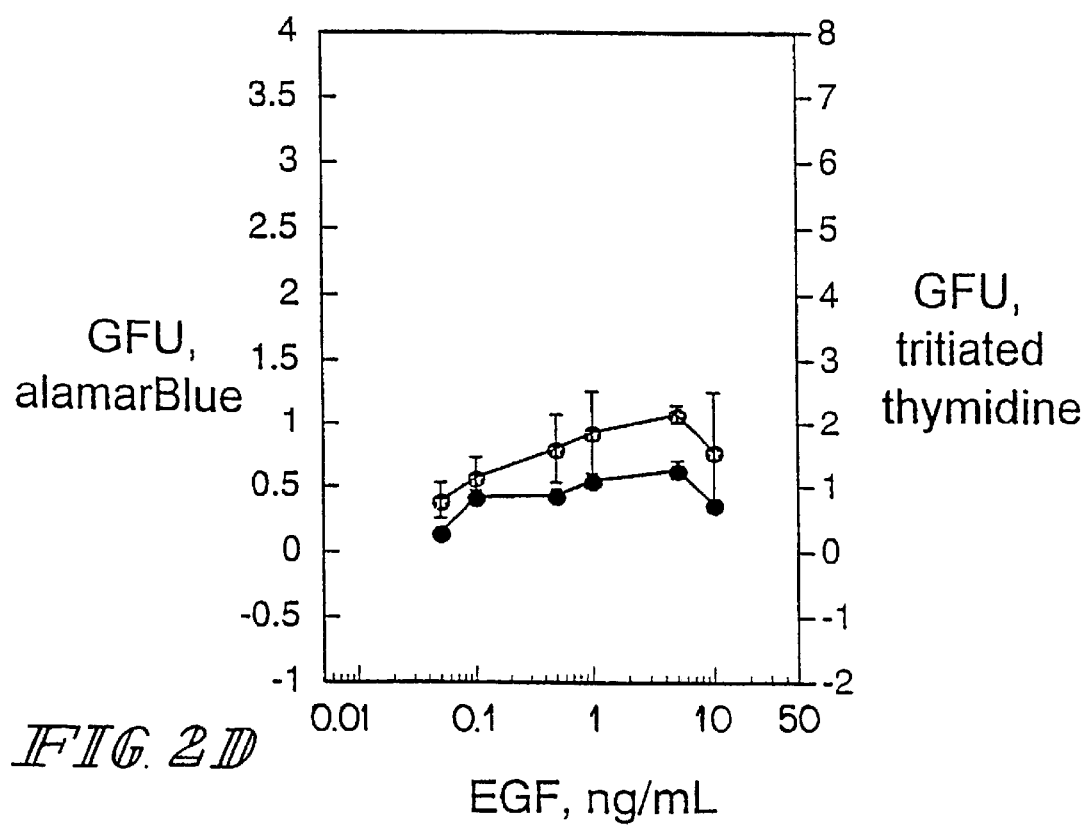

The responses of several commercially available growth factors (GF) were evaluated in the two assays, the alamar-Blue assay for whole cell proliferation (●) and [$^3$H]-thymidine incorporation assay for DNA synthesis (○), See FIGS. 2A–FIG. 2D. Each GF gave a characteristic profile of activity in the two assays. However, a general trend of higher stimulation of DNA synthesis than whole cell proliferation relative to the serum standards was seen for these purified growth factors. Porcine TGFβ1 stimulated a moderate increase in both DNA synthesis and whole cell proliferation of fibroblasts over a broad range of TGFβ1 concentrations (FIG. 2A). Purified PDGF induced a high level of DNA synthesis with little or no detectable whole cell proliferation (FIG. 2C). Purified EGF showed a dose-dependent increase in both DNA synthesis and whole cell proliferation of fibroblasts with maximal stimulation at 5 ng/mL in both assays (FIG. 2D). FGF-2 was unique among the GF tested in that its effect upon fibroblasts produced negative values in the alamarBlue assay while inducing a high level of stimulation of DNA synthesis (FIG. 2B). In both assays with FGF-2, most cells were rounded-up and had a high nuclear to cytoplasm ratio characteristic of highly stimulated cells which are unable to complete the cell cycle. This state of the cells apparently decreases the cellular metabolism necessary for the alamarBlue dye reduction and results in values less than the baseline recorded for the unstimulated (quiescent) fibroblasts.

Figure 3A:
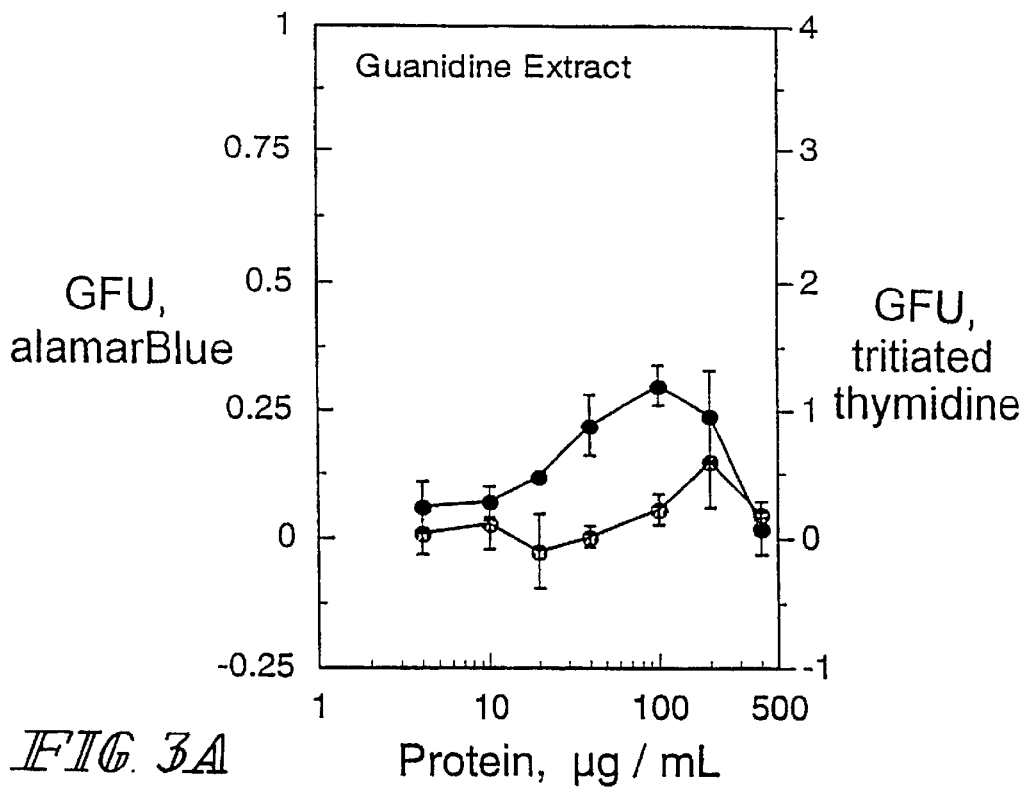
FIG. 3A–FIG. 3D. Comparison of the Effects of SIS Extracts on Fibroblasts in the Two Growth Factor Assays. Dose-response curves for extracts of SIS in alamarBlue assay (●) and [$^3$H]-thymidine assay (○) indicate the differences in range and activity of the various extracts. The intestinal submucosal tissue was extracted with either guanidine hydrochloride (FIG. 3A), urea (FIG. 3B), MgCl$_2$ (FIG. 3C) or NaCl (FIG. 3D).
Figure 3B:
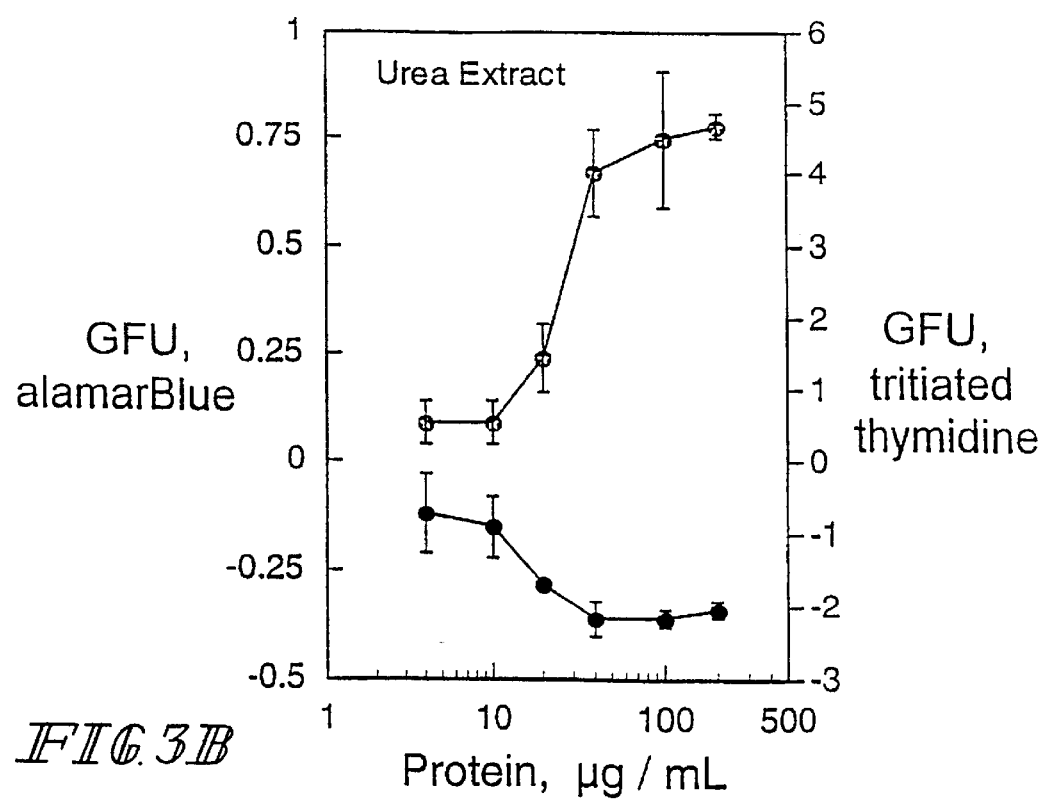
Figure 3C:
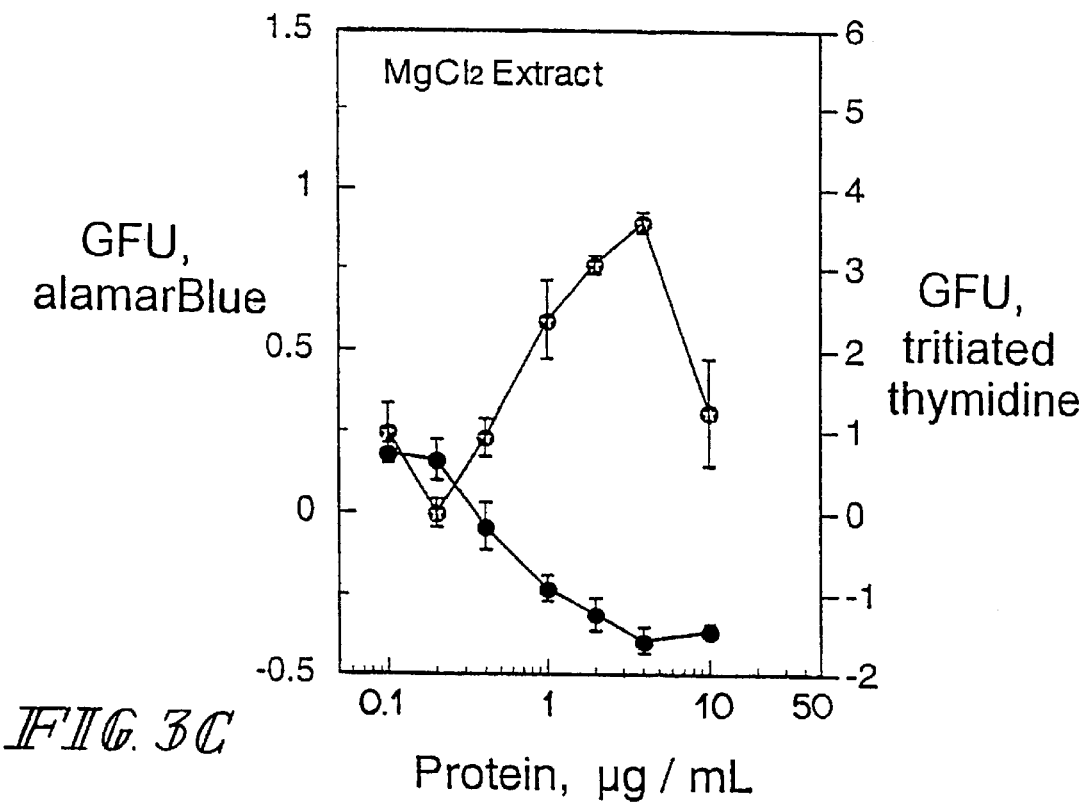
Figure 3D:
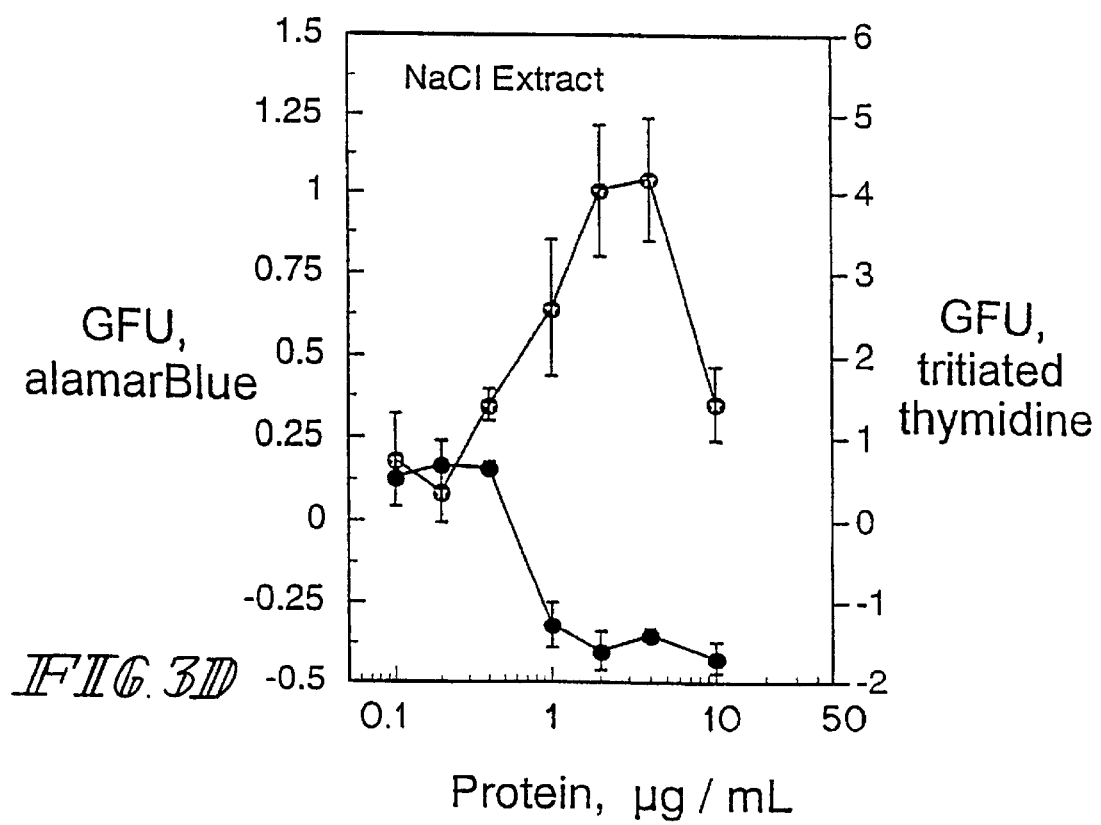

The growth factor activity of four extracts (Guanidine Hydrochloride, Urea, MgCl$_2$ and NaCl) of small intestinal tissue was analyzed in dose response curves in the two bioassays, the alamarBlue assay for whole cell proliferation (●) and [$^3$H]-thymidine incorporation assay for DNA synthesis (○), See FIGS. 3A–FIG. 3D. The activity of the guanidine extract increased with increasing dose up to 100 μg/mL in the alamarBlue assay (FIG. 3A). The activity of the same extract in the [$^3$H]thymidine assay was maximal at 200 μg/mL with a GFU value almost twice the value generated in the alamarBlue assay. The 4 M guanidine extract was unique among the extracts in its ability to generate positive values in both assays. The results with the urea extract of SIS were dramatically different. Activity of the urea extract increased with increasing dose to maximum GFU values between 4 and 5 at 400 μg/mL in the tritiated thymidine assay (FIG. 3B). In contrast the same extract gave negative GFU values in the alamarBlue assay. As was observed with FGF-2, the dose response curves in these two assays were nearly mirror images. The cellular response to the MgCl$_2$ and NaCl extracts was similar to the response seen with the urea extract (see FIG. 3C and 3D). The MgCl$_2$ and NaCl extracts were less stimulatory than the urea extract yet were active at a ten-fold lower dose range of 1 to 10 μg/mL. Total dry weight yields (Table 1) were similar (4 to 7 mg/g powdered SIS) for these water soluble extracts as were the total protein yields (2 to 4 mg/g powder). Protein content typically represented 50–70% of the extract dry weight. Extraction periods longer than 24 hours and repeat extractions were tested in an attempt to increase yields. However little or no additional activity was extractable after the initial 24 hour extraction and wash (data not shown).

TABLE 1

Total Yields of Extracts of Porcine SIS

| Extraction | Total Dry Weight mg/g powder | Total Protein mg/g powder |
| --- | --- | --- |
| 4 M Guanidine | 5.1 ± 0.5 | 3.1 ± 0.95 |
| 2 M Urea | 3.7 ± 2.2 | 2.4 ± 1.2 |
| 2 M MgCl$_2$ | 6.9 ± 3.0 | 3.95 ± 0.95 |
| 2 M NaCl | 7.7 ± 3.7 | 3.75 ± 0.75 |

Identification of FGF-2 as an Extractable Component of SIS

Figure 4:
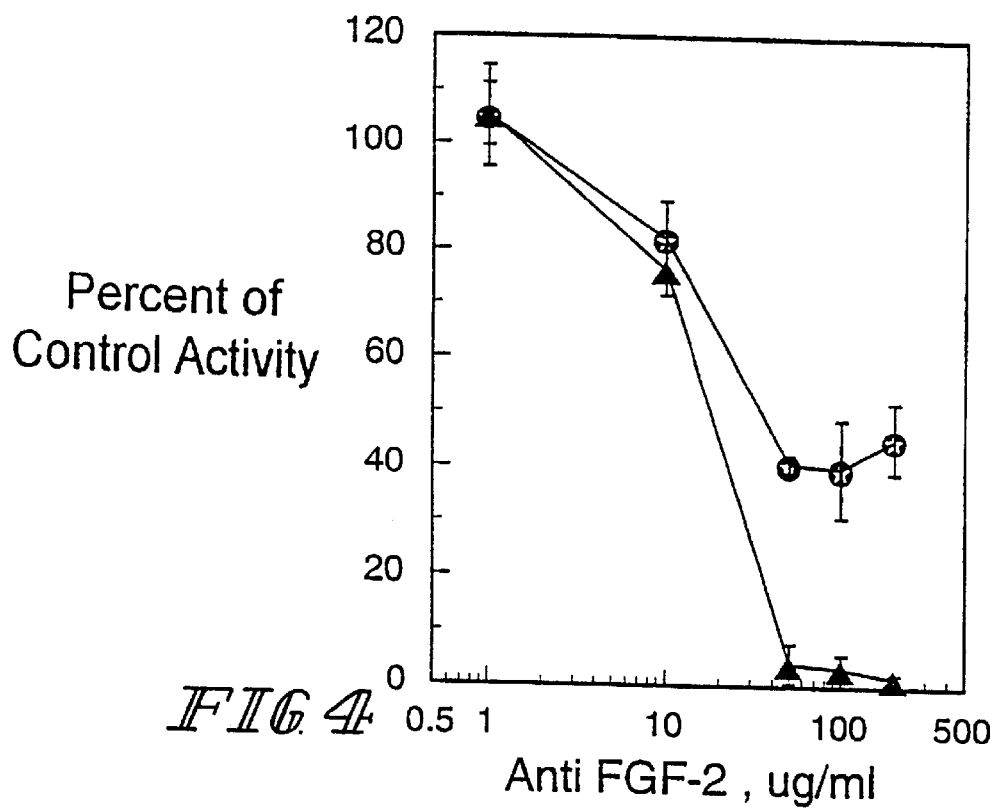
FIG. 4. Neutralization of Activity with a Growth Factor Specific Antibody. Neutralization of FGF-2 activity of standard FGF-2 (▲) and of 2 M urea extract of SIS (○) in [$^3$H]-thymidine assay. Data are the average of two experiments. Values for 100% control activities (no antibody) were 3.55±0.03 GFU at 1 ng/mL FGF-2 and 4.96±0.05 GFU at 0.2 mg/mL urea extract.

The strong similarity of the GF activity and cell morphology induced by proteins extracted from SIS with 2 M urea with those induced by purified FGF-2 suggested that FGF-2 might be a predominant GF component of this extract. This hypothesis was tested by incubating the extract with increasing amounts of a neutralizing polyclonal antibody specific for FGF-2 and determining the effect of the neutralized extract on 3T3 fibroblast cell growth. A dose dependent neutralization of GF activity of the urea extract indicated that FGF-2 was present and accounted for more than 60% of the GF activity of this extract as measured in the [$^3$H]-thymidine incorporation assay. the data from the neutralization experiments is shown in FIG. 4. Neutralization of the activity of standard FGF-2 (▲) and of 2 M urea extract of SIS (○) by the polyclonal antibody specific for FGF-2 was measured using the [$^3$H]-thymidine assay. Data are the average of two experiments. Values for 100% control activities (no antibody) were 3.55±0.03 GFU at 1 ng/mL FGF-2 and 4.96±0.05 GFU at 0.2 mg/mL urea extract.

Neutralization of the activity of the urea extract of SIS with antibody to FGF-2 was apparent also in the changes in morphology of the fibroblast cells. Swiss 3T3 fibroblasts were cultured in the presence of the extract or purchased growth factor which had been incubated either with neutralizing antibody or PBS alone. When compared to either 20% serum or the no serum control, the response of the fibroblasts to purified FGF-2 was quite distinctive showing an increased nuclear to cytoplasm ratio and a more rounded-up appearance. The cells incubated with urea extract had a similar appearance to those incubated with purified FGF-2. Neutralization of FGF-2 with anti-FGF-2 blocked the change in the cell morphology such that the cells appeared quiescent. Incubation of the urea extract with anti-FGF-2 also altered the cell morphology from that normally induced by urea extract. The appearance of the fibroblasts was that of a stimulated cell population, but unlike the appearance of the cells with serum.

The presence of FGF-2 in the urea extract of SIS was confirmed further in western blot analysis. Urea-extracted proteins of SIS were separated on 16.5% SDS-PAGE (100 μg/lane) and electro-blotted to PVDF paper. Detection of FGF-2 was with a monoclonal antibody to FGF-2 (1:10,000). Purified human recombinant FGF-2 (25 ng) was used as a standard with its mol. weight of 18 kDa. A doublet of reactive bands was reproducibly detected at approx. 19 kDa in the urea extract.

Identification of TGFβ as an Extractable Component of SIS

The extracts of SIS were screened with a neutralizing antibody specific for TGFβ isoforms (β1, β1.2, β2, β3, β5).

Figure 5:
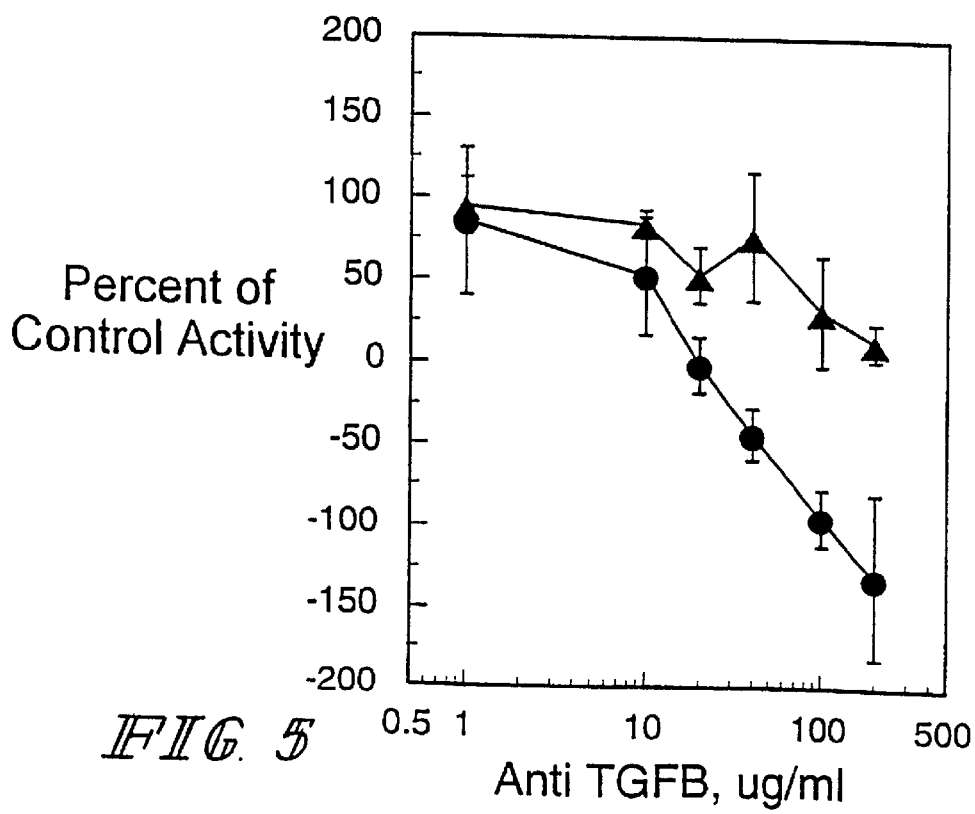
FIG. 5 Neutralization of Activity with a Growth Factor Specific Antibody. Neutralization of TGFβ activity of standard TGFβ1 (▲) and of 4 M guanidine extract of SIS (●) in alamarBlue assay. Data are the average of replicated experiments (TGFβ1, n-=2; guanidine extract, n=3). Values for 100% controls (no antibody) were 0.23±0.01 GFU at 20 pg/mL TGFβ1 and 0.15±0.05 GFU at 40 μg/mL urea extract.

GF activity was neutralized in the 4 M guanidine extract of small intestinal submucosal tissue and the standard TGFβ1 (▲), and the effect of the neutralization on 3T3 fibroblast cell growth was determined by the alamarBlue assay. The result of incubating the extract with increasing amounts of antibody was a decreasing activity which eventually reached a minimum in the negative values (FIG. 5).

The cells incubated with guanidine extract had a similar appearance to those incubated with the purified TGFβ1 but were more numerous and more extended. The response of the 3T3 fibroblasts to TGFβ1 was more subtle than the response to FGF-2, yet still evident, especially at the low cell densities of the alamarBlue assay. Cells were more flattened and spread out compared to the serum stimulated or quiescent cells. In addition, the TGFβ1 treated cells appeared less well attached to the culture dish than those cultured in the presence of the guanidine extract. Neutralization of TGFβ1 with anti-TGFβ prevented the change in morphology of the quiescent cells, but after neutralization of the guanidine extract with anti-TGFβ, the cells still appeared to have a different morphology than quiescent cells with many of the cells taking on an elongated, spindle shaped appearance.

An affinity-purified polyclonal antibody which was reactive against TGFβ1, β2, β3 and β5 was used to probe for TGFβ in the guanidine extract. No protein band was detected at 25 kDa, a molecular weight corresponding to that of the non-reduced purified TGFβ1, β2, and β3 standards. However, higher molecular weight protein bands of the guanidine extract were reactive with this antibody. These bands were also detected in a partially purified fraction of the guanidine extract. Guanidine extracts of demineralized bone powder, a known source of TGFβ, yielded an identifiable 25 kDa protein band along with several higher mol. wt. bands (See FIG. 6). No bands were detected in the controls with secondary antibody only (data not shown).

Discussion

There is increasing evidence suggesting that growth factors, in particular FGF-2 and TGFβ, are also components of extracellular matrices. TGFβ has been reported to be stored in bone matrix through an association with decorin, a proteoglycan component of the extracellular matrix. Binding to decorin has been shown to regulate the bioactivity of TGFβ. In other studies, TGFβ has been co-localized with decorin to the extracellular matrix of various developing tissues. FGF-2 is dependent on binding to heparan sulfate, a glycosaminoglycan (GAG), for high affinity binding to its receptor. Specific binding to perlecan, a heparan sulfate proteoglycan of the basement membrane/extracellular matrix, has suggested a possible storage site in the extracellular matrix for FGF-2. In addition, both FGF-2 and TGFβ, along with EGF, PDGF and IGF-1, were identified in extracts of basement membrane/extracellular matrix of Engelbreth-Holm-Swarm mouse tumor.

Growth factors have been identified in gastrointestinal tissues previously. Nice and co-workers (see J. Biol. Chem. 266: 14425–14430) isolated a N-terminally extended form of FGF-2 from porcine colonic mucosa. TGFα and EGF were found to be present in colonic mucosa albeit at significantly lesser quantities. However, the present study is the first demonstration of growth factors within the submucosal tissue of the intestine and specifically in the extracellular matrix portion of this tissue.

Among the presently characterized growth factors, FGF-2 and TGFβ have been identified as particularly important to wound healing and tissue remodeling. Both FGF-2 and TGFβ have been shown to play multiple significant roles in stimulating neovascularization processes and regulating cellular activities during wound healing. For example, FGF-2 promotes mesenchymal cell migration and proliferation to accelerate healing of gastric mucosa and calvarian bone. TGFβ stimulates healing of occasional wounds through potent chemotactic activity and through modulation of gene expression of several extracellular matrix components. In addition, both factors have been shown to be involved in wound contraction. Perhaps the most extensively studied role of these two growth factors has been in the area of angiogenesis. The regulation of the proteolytic activity responsible for the matrix remodeling that is necessary for vascular ingrowth is dependent on the balance of stimulatory (FGF-2) and inhibitory (TGFβ) factors.

Events of the remodeling response induced by SIS are similar to those of fetal wound healing and embryogenesis and include rapid neovascularization, cellular migration, proliferation, differentiation, and heightened biosynthesis of extracellular matrix components. The inductive properties of SIS suggest that the biomaterial either contains active growth factors or is able to induce a rapid stimulation of growth factor production by the host tissue, or both. The characterization of protein extracts of SIS revealed a significant amount of growth factor activity present in the tissue. The varied responses of different extracts suggested the possibility of several growth factors being present and analysis of the bioactivity associated with various extract fractions has identified a TGFβ-related and FGF-2 component. Although maximal neutralization with anti-FGF-2 demonstrated that this growth factor was responsible for the majority of the measurable activity of the urea extract, considerable GF activity remained. This activity is yet to be identified. Likewise, residual activity was observed when the TGFβ activity of the guanidine extract was completely neutralized. The negative values observed after TGFβ neutralization (in the alamarBlue assay) suggested the presence of FGF-2 activity which might have been previously masked by the TGFβ-related activity. However, dual neutralization of the guanidine extract with antibodies to both TGFβ and FGF-2 revealed that FGF-2 was not responsible for the residual activity. The presence of an inhibitory molecule (e.g. Decorin) which was masked by the TGFβ stimulatory activity in this complex extract appears likely.

The polyclonal antibody used to detect TGFβ recognized several protein bands in guanidine extract of submucosal tissue at molecular weights considerably higher than observed for purified TGFβ standards (25 kDa) or extract of bone. It is not clear which, if any, of these proteins are responsible for the TGFβ-related activity of guanidine extract of the submucosal tissue. That one of the previously reported isoforms of TGFβ is present in the guanidine extract of small intestinal submucosa, but at a level below detection by the western blot, is still a possibility. However, initial separation of proteins of the guanidine extract of small intestinal submucosa with gel filtration chromatography, based on a protocol for isolating TGFβ [Yamaguchi et al., 1990], also did not reveal a 25 kD band but did demonstrate that the antibody-reactive higher molecular weight proteins stay with the TGFβ neutralizable activity through one step of purification. Accordingly, submucosal tissue may contain a very low level of one of the known isoforms of TGFβ, a yet unidentified form of TGFβ or a novel TGFβ-like GF.

EXAMPLE 2

Extraction of Glycosaminoglycans

Materials and Methods

Reagents. Standard preparations of chondroitin sulfate A (CSA), chondroitin sulfate B (CSB), chondroitin sulfate C (CSC), hyaluronic acid (HA), and heparin (HEP) were purchased from Sigma, St. Louis, Mo. Heparan sulfate (HS) standard was purchased from ICN Pharmaceuticals, Costa Mesa, Calif. Type MV bacterial protease, Hyaluronidase (E.C. 4.2.2.1), Chondroitinase AC (E.C. 4.2.2.5), Chondroitinase B (no E.C. number), Heparinase I (E.C. 4.2.2.7) and Heparinase III (E.C. 4.2.2.8) were purchased from Sigma, St. Louis, Mo. Titan III cellulose acetate membranes were purchased from Helena Labs, Beaumont, Tex.

Extraction of GAGs from SIS. Glycosaminoglycans were extracted from porcine SIS following the method of Breen, et.al. [Methods in Carbohydrate Chemistry, Vol. 7, New York: Academic Press 1976, pp 101–115.] with minor modifications. Briefly, samples of SIS were frozen in liquid nitrogen, pulverized using a mortar and pestle, and then lyophilized. The SIS powder was weighed and was placed in a solution of chloroform-methanol at 4° C. for 24 hours with constant stirring. After 24 hours, the liquid was poured off, the chloroform-methanol solution was changed, and the procedure was repeated. After 48 hours, the suspension was centrifuged at 1400 g (Beckman model GPR) for 20 minutes and the supernatant was discarded. The resulting precipitate was dried under vacuum pressure and was stored at $-20°$ C. until further use.

Each 50 mg sample of dried, defatted tissue was resuspended in 2 ml of 0.5M sodium acetate buffer (pH 7.5), placed in a boiling water bath for 20 minutes and incubated with protease (5 $\mu$g/mg tissue) for 12 hours at 37° C. Additional enzyme was added to the digest to yield a concentration of 10 $\mu$g/mg tissue, and digestion was allowed to proceed for 48 more hours. 10 mM calcium chloride was added to the digest to yield a calcium concentration of 1.0 mM, and the samples were placed in a shaking incubator at 50° C. for 24 hours. The tissue digest was cooled to 4° C. and trichloroacetic acid was added to a final concentration of 5%. The solution was allowed to sit for 10 minutes before being centrifuged at 17,300 g (Beckman model J2-21) and 4° C. for 20 minutes. The supernatant was saved and the precipitate was treated with 2 ml of 5% trichloroacetic acid and recentrifuged. The supernatants were pooled and were treated for 24 hours at 4° C. with three volumes of 5% potassium acetate in 100% ethanol. The suspension was centrifuged for 20 minutes at 17,300 g and 4° C. and the supernatant was discarded. The precipitate was treated sequentially with 2 ml of 100% ethanol, 2 ml of a 1:1 v/v mixture of ethanol-ether, and 2 ml of 100% ether (with centrifugation between treatments). The ether was removed under continuous positive pressure air flow. The dried precipitate was resuspended at a concentration of 2 mg/ml in 0.075 M NaCl for immediate use, or was stored dry at $-20°$ C.

Quantitation of GAG Amount. The total amount of GAGs in SIS isolate was evaluated according to the uronic acid analysis developed by Blumenkrantz and Asboe-Hansen [*Anal. Biochem* 54, 484, 1973.] with minor modifications. Briefly, 200 $\mu$l of a sample of SIS isolate (2 mg/ml in 0.075 M NaCl) was added to 1.2 ml of 0.0125 M potassium tetraborate in concentrated sulfuric acid. The mixture was heated to 100° C. for 5 minutes and was cooled in ice water. The cooled samples were treated with 20 $\mu$l of a solution of 3 mg m-hydroxydiphenyl in 10 ml of 0.5 N NaOH. Absorbance was read at 520 nm. (Perkin Elmer Lambda 3B spectrophotometer) after ten minutes.

Enzyme Degradation of Isolated GAG Chains: Enzymatic degradation of GAG chains was performed using the general procedures reported by Breen, et al, [See above] and Linhardt. [Current Protocols in Molecular Biology, New York, N.Y.; Wiley and Sons, 1994, Unit 17.13B; Zohse et al, *J. Biol* Chem 267, 24347, 1992] A sample of GAG isolate was resuspended at 2 mg/ml in 0.075 M NaCl and 50 $\mu$l aliquot of the solution were treated with enzyme as described below.

Digestion with Hyaluronidase. The GAG isolate was suspended in 50 $\mu$l of sodium acetate sodium chloride buffer, pH 5.4, containing 0.15 M each of sodium acetate and sodium chloride and 0.07 units of hyaluronidase. The solution was incubated for 1 hr at 37° C. in a shaking water bath. The solution was boiled for 1 minute to denature the enzyme and was then cooled to room temperature for electrophoresis.

Digestion with Chondroitinase AC and Chondroitinase B. The GAG isolate was suspended in 50 $\mu$l of Tris-chloride-acetate buffer containing 0.05 M each of Tris, sodium acetate, and sodium chloride, adjusted to pH 8.0. To the buffer were added 1.5 $\mu$moles of albumin and 0.07 units of enzyme. The solution was incubated for 1 hr at 37° C. in a shaking water bath. The solution was boiled for 1 minute to denature the enzyme and was then cooled to room temperature for electrophoresis.

Digestion with Heparinase I and III. The GAG isolate was suspended in 50 $\mu$l of 5 mM sodium phosphate buffer, pH 7.6, containing 200 mM sodium chloride, 0.01% (w/v) albumin and 3.75 units of enzyme. The solution was incubated for 8 hr at 30° C. in a shaking water bath. The solution was boiled for 1 minute to denature the enzyme and was then cooled to room temperature for electrophoresis.

Electrophoretic Separation of Isolated GAGs. Electrophoresis was performed on Titan III cellulose acetate membranes. Each membrane was immersed in water to a height of 1.5 cm, and the opposite end was immersed in the buffer to be used during the run. A thin 2–4 mm band was left between the buffer soak and the water soak. Samples (2 mg/ml) containing a trace of phenol red were applied to the membrane in 1.0 $\mu$l aliquot. The membrane was placed in the electrophoresis chamber and was subjected to a constant voltage of 200V for 2–3 minutes, until a thin, yellow line was visible at the boundary between the buffer and the water. The plate was then submerged in the electrophoresis buffer and allowed to soak for two minutes.

Electrophoresis was performed in one of three different buffer systems to optimally separate the different GAG species. Electrophoresis using a 0.05 M LiCl –0.01 N HCl buffer (pH 2.0, 20 min, 12 mA) was used to separate the chondroitin sulfate group of GAGs from heparan sulfate, heparin, and hyaluronic acid. It was possible to separate chondroitin sulfate A from the other GAGs in the tissue using a 0.05 M phosphate buffer system (pH 7.2, 15 min, 10 mA). The presence of hyaluronic acid and chondroitin sulfate B were confirmed using a buffer system containing 0.2 M ZnSO4 (pH 5.1,75 min, 6 mA).

Following electrophoresis, the separated GAGs were stained using a 10% solution of alcian blue in 3% acetic acid (pH 2.5) for 10 minutes. After blotting excess 25 stain, the membrane was destained for 5 minutes in an aqueous solution containing 5% acetic acid and 10% ethanol. If the background was not clear, the destaining solution was changed and the procedure repeated. The membrane was dried in room air under a ventilated hood at 25° C.

Results

The GAG isolation protocol yielded 3.5±1.3 mg of extract from each 50 mg sample of dried, defatted SIS. Analysis of the uronic acid present in the isolated sample showed that the uronic acid content of the extract was 47.7 $\mu$mol/g dry tissue weight. These values correspond to a total GAG content of 21 $\mu$g/mg of the dry weight of the porcine SIS tissue. The identical procedures performed using canine aorta as the source tissue yielded values for uronic acid of 28.2 μmol/g (12.4 μg GAG/mg dry tissue). These values correlate well with reports of GAG amounts in other tissues.

Following extraction, GAGs were separated and identified using cellulose acetate electrophoresis. Because the structural differences in GAG types cause different GAG species to migrate at different rates in different buffer systems, three different buffer systems were used to optimally separate and identify all of the GAG types in the extraction mixture. A LiCl buffer system was used to separate HS, HEP, and HA from the chondroitin sulfates, and a phosphate buffer system was used to separate the chondroitin sulfate groups from each other. It should be noted that the presence of chondroitin sulfate B was confirmed using a buffer system containing zinc sulfate, because CSB and HEP migrate similarly in the phosphate buffer.

Following initial separation and identification, GAG types were confirmed using selective enzyme digestion and comparative electrophoresis. Samples of extracts were subjected to treatment with heparinase or heparitinase. Using a LiCl buffer system for electrophoresis, it was possible to confirm the presence of heparin and heparan sulfate in the SIS-derived sample.

Although heparinase and heparitinase selectively cleave heparin and heparan sulfate GAG chains, they are not totally selective for one GAG species or the other. The primary substrate for heparinase is heparin, while the primary substrate for heparitinase is heparan sulfate. Because of the similarity in structure of the GAG chains, cross-digestion occurs. Evidence of cross-digestion can be seen but it does not interfere with the interpretation of the results.

A $ZnSO_4$ buffer system was used to confirm the presence of CSB and HA in the SIS isolate. To prove the presence of CSB in the matrix, a sample of GAG extract was treated with chondroitinase B, an enzyme selective for the chondroitin sulfate B GAG chain; it does not digest CSA or CSC. Hyaluronidase treatment of an SIS extract similarly confirmed the presence of HA in the material. It should be noted that is not possible to separate CSA and HEP in this buffer system because of the similarity in their mobilities.

A phosphate buffer system was used to separate CSA from the other components in the SIS-GAG isolate. To confirm the presence of this GAG in the material, the sample was treated with chondroitinase AC. This enzyme selectively digests the CSA and CSC GAG chains, but leaves CSB intact. In addition to confirming the presence of CSA in the material, it was also possible to determine that CSC was absent from the SIS-GAG isolate.

Discussion of Results

The analysis of uronic acid or hexosamine is recommended as the method of choice for obtaining the total GAG concentration of an unknown sample. We have quantitated the uronic acid content of porcine SIS and have determined it to be 47.7 μmol/mg dry tissue weight. This value corresponds to a total GAG content in the tissue of 21 μg/mg dry tissue weight. We have also determined that five different species of GAGs contribute to this total amount. These GAGs are chondroitin sulfate A, chondroitin sulfate B, heparin, heparan sulfate, and hyaluronic acid. The relative amounts of the different species were not determined in the present study.

Since SIS represents a specific trilaminate structure of the small intestine, the composition of SIS must be established independently from any other reports specifying the overall GAG content of hog intestine. These experiments indicate that several types of GAGs are present in SIS, a structure which consists of the tunica submucosa, the tunica muscularis mucosa, and the less well developed stratum compactum.

It is not surprising that a wide variety of GAG types are found in this tissue since the structure, especially the superficial layers, essentially serves as the basement membrane for the rapidly dividing cell population of the tunica mucosa. The amount of GAG in SIS corresponds well with the amounts reported in other basement membrane containing tissues, such as canine meniscal tissue and adult sclera. Adult cornea, which consists almost entirely of basement membrane, contains significantly more GAGs, while skin contains significantly less.

EXAMPLE 3

Extraction of Fibronectin

Fibronectin (Fn) is a large dimeric protein of the plasma and extracellular matrix with a molecular weight of approximately 440 kDa. Fn is among the first proteins deposited in new extracellular matrix and has chemotactic and cell adhesive activities for a variety of cells, including fibroblasts and endothelial cells. As these cells are important in wound healing and tissue remodeling, Fn may play a pivotal role in the recruitment and retention of host cells to the wound site.

Protocol/Results

Localization of Fn within porcine SIS was achieved by immunohistochemical staining of frozen sections. The Fn content of SIS was quantitated by a competitive ELISA technique. Protein extracts of SIS prepared by extraction with chaotropic buffers containing heparin were analyzed for Fn content. After three extractions, collagenase digestion of the tissue was employed to disrupt the non-Fn matrix and solubilize any remaining extractable protein. Finally, Fn was extracted from SIS and purified by affinity chromatography for characterization with respect to porcine and human plasma fibronectins by SDS-PAGE and Western blot analysis.

The procedure used for extraction of fibronectin from SIS is as follows:

Weigh ground, frozen SIS into tared container.

Add 4 ml of extraction buffer per gram of tissue. Extraction buffer contains 2 M urea, 2.5 mg/ml heparin, 50 mM Tris, at pH 7.5.

Stir on magnetic stirrer overnight at 4° C. Add protease inhibitors (PMSF, NEM, and benzamidine) to make 1 mM of each.

Centrifuge to pellet residual tissue. Collect supernatant.

May repeat extraction with urea/heparin/protease inhibitors to improve yield of extracted fibronectin.

Dialyze extract against tris-buffered saline or phosphate-buffered saline to remove extraction agents.

Store at 4° C.

Fibronectin can be purified from the dialyzed extract using affinity chromatography, with gelatin-Sepharose (Pharmacia) gel, following method of Vuento and Veheri [*Biochemical Journal* 183:331–332, 1979]. The Fn concentration in the dialyzed extracts or purified protein can be determined by an ELISA method.

Immunohistochemical staining showed homogeneous Fn presence throughout the thickness of the SIS tissue. There was no obvious specific localization to, or greater concentration in, any layer or structure. This was consistent with whole pig intestine, which exhibited Fn staining in essentially all extracellular spaces in the areas from which SIS is derived. ELISA revealed that Fn concentration was greatest in the first tissue extract, decreased in the second, and was negligible in the third. Collagenase digestion did not release significantly more Fn that the extraction procedures. The Fn content is estimated at 0.1% of the dry mass of SIS. SDS-PAGE and Western blot analysis revealed identity to anti-Fn antibodies of all proteins tested.

EXAMPLE 4

In-Vitro Cell Stimulating Activity of Submucosal Tissue Extracts

The ability of stomach submucosa, urinary bladder submucosa and intestinal submucosa (or components thereof) to cause cell proliferation was measured in-vitro by two assays that have been developed in our laboratory. One assay involved the use of alamar blue, an indicator of whole cell proliferation. The second assay involved the incorporation of tritiated thymidine into a population of 3T3 fibroblasts. This second assay is indicative of the degree of DNA Synthesis (which does not always correlate with whole cell proliferation). The assays were conducted as described in Example 1. The combined use of both of these in-vitro assays yields complementary information regarding the ability of materials to cause, DNA synthesis and/or cell-proliferation.

Figure 7:
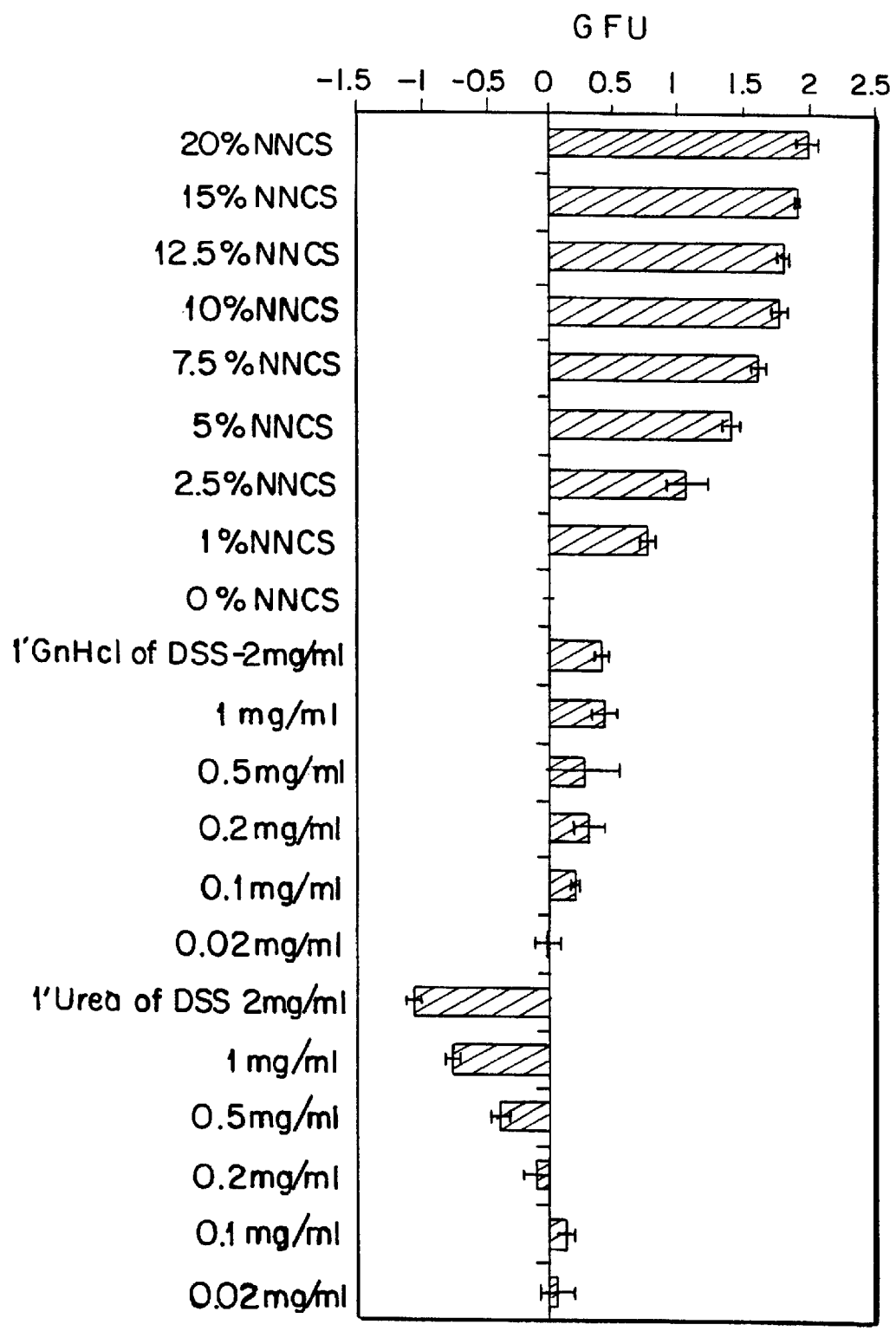
FIG. 7. Effects of Stomach Submucosal Tissue on 3T3 Fibroblast Cell Growth. The response of fibroblast cells to a urea (1'Urea of DSS) or guanidine hydrochloride extract (1'GnHcl of DSS) of stomach submucosal tissue was determined using the alamarBlue assay. Neonatal Calf Serum (NNCS) was used as a control to establish a standard curve dose response of the 3T3 cells to growth factors known to be present in the NNCS, and the results are expressed as relative growth factor units, GFU.

In one experiment, the results of which are shown in FIG. 7, stomach submucosal tissue was subjected to two different extraction procedures and the resulting extracts were evaluated for their effects on Swiss 3T3 fibroblasts. The stomach submucosal tissue was extracted with either urea or guanidine hydrochloride according to the procedures described in Example 1. Each of these extraction procedures has the ability to differentially extract components from the submucosal tissue. For example, TGFβ can be extracted from intestinal submucosal tissue more efficiently with the guanidine hydrochloride method whereas FGF can be extracted more efficiently with the urea method.

The response of fibroblast cells to a urea or guanidine hydrochloride extract of stomach submucosal tissue was determined using the alamarBlue assay (FIG. 7). Neonatal Calf Serum (NNCS) was used as a control to establish a standard curve dose response of the 3T3 cells to growth factors known to be present in the NNCS. The results are expressed as relative growth factor units, GFU. Activity of the guanidine hydrochloride extract (1'GmHcl of DSS) increased with increasing extract dose to maximum GFU values of approximately 0.5. In contrast, the urea extract (1'Urea of DSS) gave increasingly negative GFU values with increasing extract dose.

Figure 8:
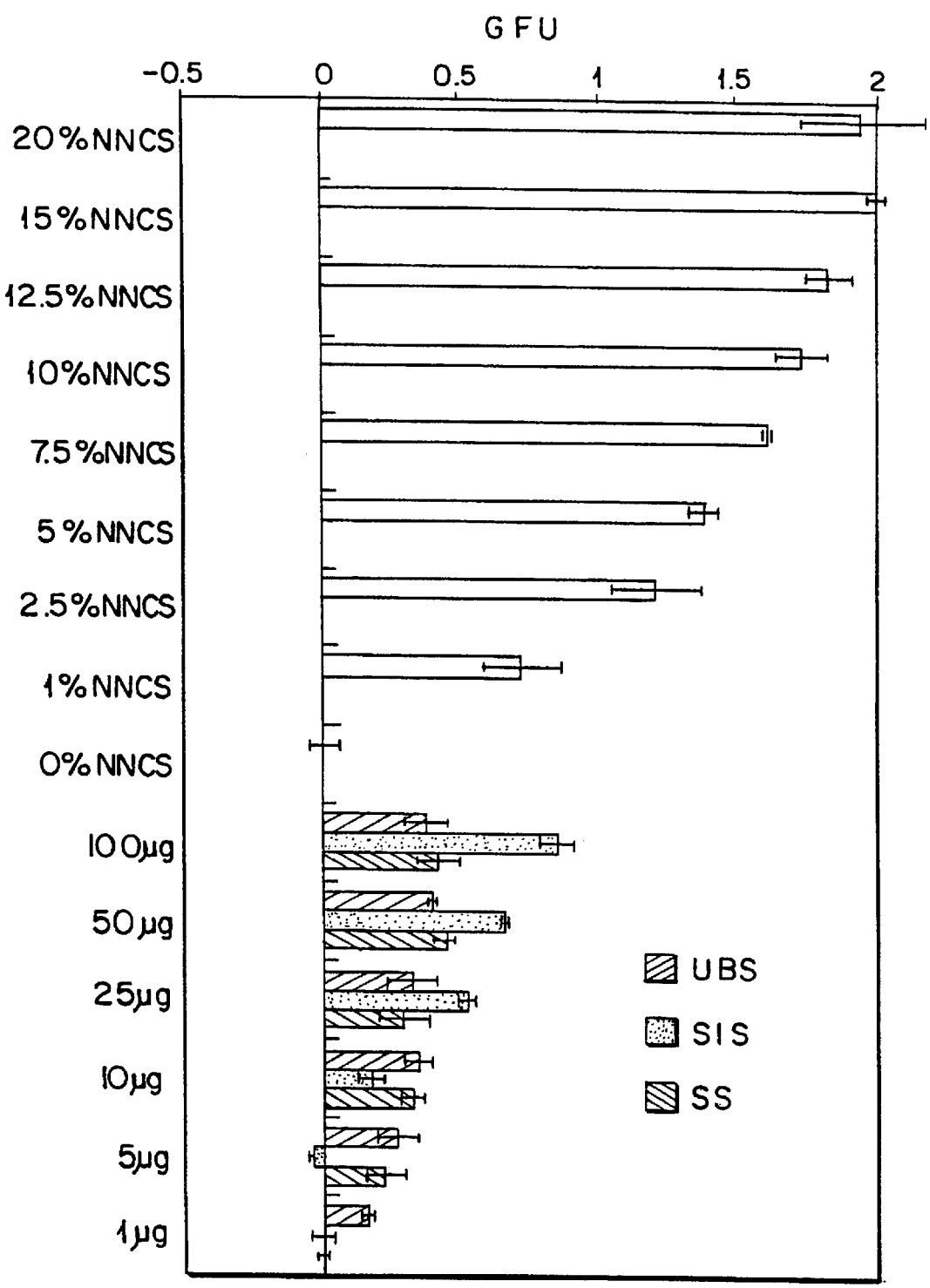
FIG. 8. Comparison of the Response of 3T3 Fibroblasts to Stomach Submucosa (SS), Small Intestinal Submucosa (SIS), and Urinary Bladder Submucosa (UBS) extracts. Neonatal Calf Serum (NNCS) was used as a control to establish a standard curve dose response of the 3T3 cells to growth factors known to be present in the NNCS, and the results are expressed as relative growth factor units, GFU.
Figure 9:
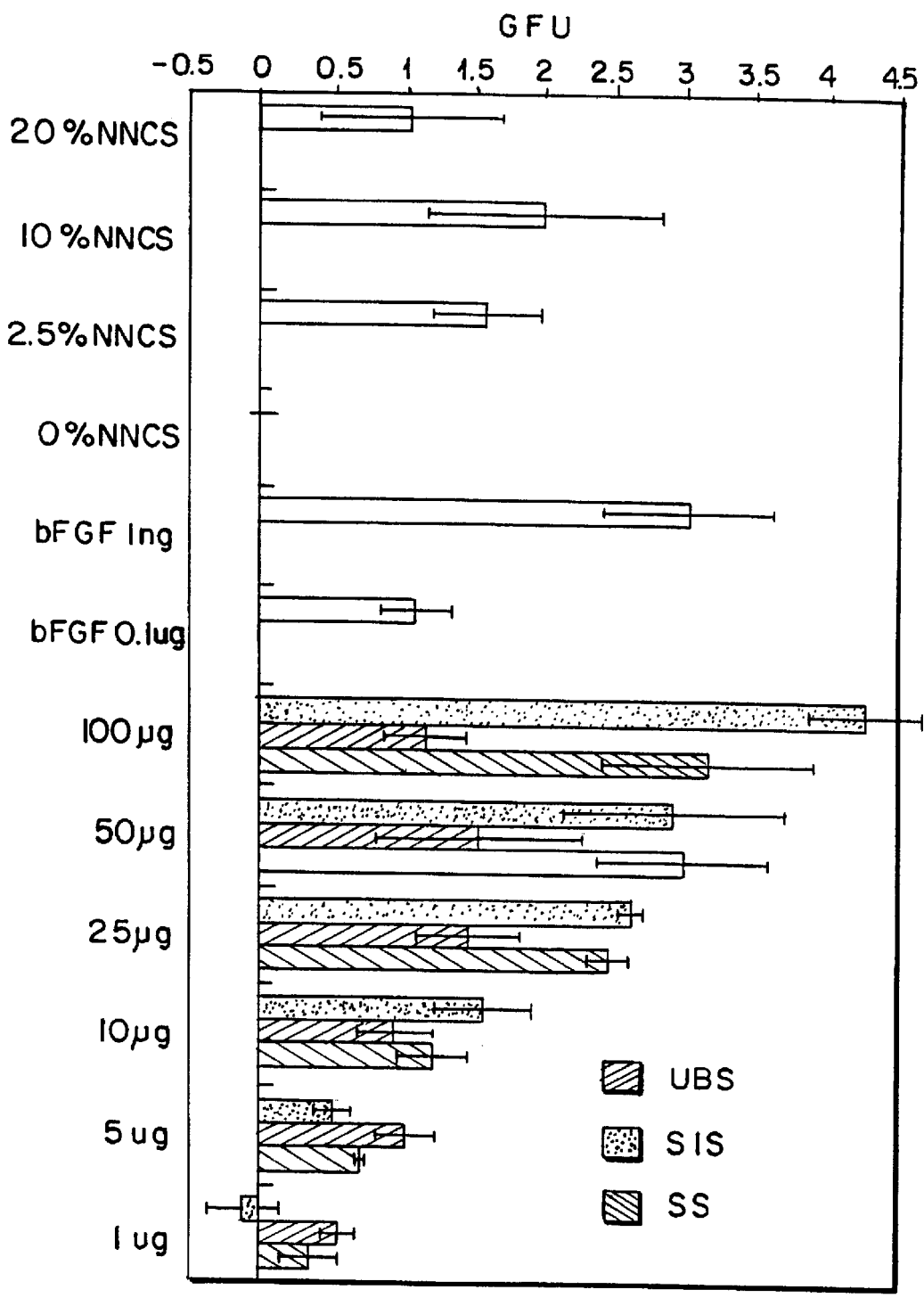
FIG. 9. Comparison of the Response of 3T3 Fibroblasts to Stomach Submucosa (SS), Small Intestinal Submucosa (SIS), and Urinary Bladder Submucosa (UBS) extracts. Neonatal Calf Serum (NNCS) was used as a control to establish a standard curve dose response of the 3T3 cells to growth factors known to be present in the NNCS, and the results are expressed as relative growth factor units, GFU.

In a second experiment, the response of 3T3 fibroblast cells to extracts prepared from were compared. The effects of various concentrations of a guanidine hydrochloride extract of the respective three tissues on 3T3 fibroblast cell growth was determined using the alamarBlue assay (FIG. 8). In addition, the response of 3T3 fibroblasts to various concentrations of a urea extract of the respective three tissues was determined using the tritiated thymidine assay (FIG. 9). It is obvious from these data that a guanidine hydrochloride extract of all three biomaterials causes cell proliferation in the alamar blue assay, with SIS showing the greatest degree of cell proliferation and SS and UBS showing lesser, but still positive activity. The urea extract of all three biomaterials causes DNA synthesis in the 3T3 cells with SS showing the greatest degree of DNA synthesis, SIS the second and UBS with the least (but still positive) at 100 μg concentration of extract.

What is claimed is:

1. A method for preparing a bioactive composition useful for promoting cell growth comprising the steps of extracting submucosal tissue with an aqueous solution of extraction excipients to form an aqueous solution of extracted bioactive components and extraction excipients, and separating the extracted bioactive components from at least a portion of the extraction excipients to form the bioactive composition.

2. The method of claim 1 wherein the aqueous solution of extracted bioactive components is enriched in at least one of the bioactive components to provide an enriched extract having multiple components.

3. The method of claim 1 or claim 2 wherein the submucosal tissue is selected from the group consisting of intestinal submucosa, stomach submucosa, urinary bladder submucosa, and uterine submucosa.

4. The method of claim 1 or 2 wherein the extraction excipient is selected from the group consisting of chaotropic agents, enzymes and enzyme inhibitors.

5. The method of claim 1 or 2 wherein the extraction excipients comprise a chaotropic agent.

6. The method of claim 5 wherein the chaotropic agent is selected from urea, guanidine, sodium chloride, magnesium chloride, and ionic or non-ionic surfactants.

7. The method of claim 5 wherein the extraction excipient solution further includes at least one protease inhibitor.

8. The method of claim 1 or 2 wherein the step of separating the extracted bioactive components from at least a portion of the extraction excipients includes the step of dialyzing the aqueous solution of the extracted bioactive components and the extraction excipients.

9. The method of claim 8 further comprising the step of lyophilizing the dialyzed solution.

10. An isolated extract of vertebrate submucosa comprising a solution of bioactive components extracted from native vertebrate submucosa and substantially free of extraction excipients.

11. The isolated extract of claim 10 wherein the solution of bioactive components is enriched in at least one of the bioactive components to provide an enriched extract having multiple components.

12. The isolated extract of claim 11 wherein the enriched bioactive component is a growth factor.

13. The isolated extract of claim 12 wherein the enriched bioactive component is a TGFβ-related protein or fibroblast growth factor.

14. The isolated extract of claim 11 wherein the enriched bioactive component is fibronectin.

15. The isolated extract of claim 11 wherein the enriched bioactive component is a glycosaminoglycan.

16. The isolated extract of claim 11 wherein the enriched bioactive component is chondroitin sulfate A or chondroitin sulfate B.

17. The isolated extract of claim 11 wherein the enriched bioactive component is heparin, heparan sulfate or hyaluronic acid.

18. The isolated extract of claim 10 wherein the extract is in the form of a dry powder or lyophilizate.

19. The isolated extract of claim 10 wherein the extract is in the form of a cream.

20. An isolated extract of intestinal vertebrate submucosa comprising a solution of bioactive components extracted from native intestinal vertebrate submucosa and substantially free of extraction excipients.

21. A method of manufacturing an extract enriched for a bioactive component of submucosal tissue of a warm blooded vertebrate, said method comprising the steps of extracting the submucosal tissue with an aqueous solution of extraction excipients to form an aqueous solution of extracted bioactive components and extraction excipients, and separating the extracted bioactive components from the extraction excipients to form a bioactive extract.

22. A composition prepared in accordance with the process of claim 2.

23. A method of preparing a cell growth medium comprising the method of claim 1 further comprising the step of adding the bioactive composition to a cell growth medium.

24. A method of promoting wound healing with a bioactive composition prepared in accordance with the method of claim 1 comprising the step of contacting a wound with an amount of the bioactive composition effective to promote wound healing.

25. The isolated extract of claim 11 wherein the enriched bioactive component is a protein.

26. The isolated extract of claim 11 wherein the enriched bioactive component is an extracellular matrix component.

27. The isolated extract of claim 20 wherein the solution of bioactive components is enriched in at least one of the bioactive components to provide an enriched extract having multiple components.

* * * * *